United States Patent
Eisenkraetzer et al.

(10) Patent No.: US 11,473,042 B2
(45) Date of Patent: Oct. 18, 2022

(54) MONITORING STATE DEVIATIONS IN BIOREACTORS

(71) Applicant: Hoffmann-La Roche, Inc., Little Falls, NJ (US)

(72) Inventors: Detlef Eisenkraetzer, Iffeldorf (DE); Christian Klinger, Penzberg (DE); Katrin Greppmair, Penzberg (DE); Claudia Schmidberger, Staig (DE)

(73) Assignee: Hoffmann-La Roche, Inc., Little Falls, NJ (US)

( * ) Notice: Subject to any disclaimer, the term of this patent is extended or adjusted under 35 U.S.C. 154(b) by 1238 days.

(21) Appl. No.: 15/765,208

(22) PCT Filed: Oct. 28, 2016

(86) PCT No.: PCT/EP2016/076167
§ 371 (c)(1),
(2) Date: Mar. 30, 2018

(87) PCT Pub. No.: WO2017/072340
PCT Pub. Date: May 4, 2017

(65) Prior Publication Data
US 2018/0273885 A1 Sep. 27, 2018
US 2019/0367854 A9 Dec. 5, 2019

(30) Foreign Application Priority Data
Oct. 30, 2015 (EP) .................................. 15192387

(51) Int. Cl.
C12M 1/34 (2006.01)
C12M 1/36 (2006.01)
G01N 27/404 (2006.01)

(52) U.S. Cl.
CPC ............... *C12M 1/34* (2013.01); *C12M 1/36* (2013.01); *C12M 41/26* (2013.01); *C12M 41/34* (2013.01); *C12M 41/48* (2013.01); *G01N 27/404* (2013.01)

(58) Field of Classification Search
None
See application file for complete search history.

(56) References Cited

U.S. PATENT DOCUMENTS

| 4,513,280 | A | 4/1985 | Hannan et al. |
| 2010/0184147 | A1 | 7/2010 | Cheng et al. |
| 2014/0330398 | A1 | 11/2014 | Fan et al. |
| 2015/0299688 | A1 | 10/2015 | Da Silva Ribeiro et al. |

FOREIGN PATENT DOCUMENTS

| CN | 1557948 A | 12/2004 |
| EP | 0147975 A2 | 7/1985 |
| EP | 2365060 A1 | 9/2011 |
| JP | S60-141286 A | 7/1985 |
| JP | 2011-160802 A | 8/2011 |
| JP | 2014-527824 A | 10/2014 |
| WO | WO-2007/085880 A1 | 8/2007 |
| WO | WO-2013/041487 A1 | 3/2013 |

OTHER PUBLICATIONS

Gramer, M.J., et al., "A semi-empirical mathematical model useful for describing the relationship between carbon dioxide, pH, lactate and base in a bicarbonate-buffered cell-culture process," Biotechnology and Applied Biochemistry, vol. 47 (No. 4), 197-204 (2007).
Japanese Notice of Reasons for Rejection for Japanese Patent Application No. 2018-517792, dated Nov. 30, 2020, (18 pages), Japanese Patent Office.

*Primary Examiner* — Joseph Woitach
(74) *Attorney, Agent, or Firm* — Alston & Bird LLP

(57) ABSTRACT

The invention relates to a system (100) for monitoring deviations of a state of a cell culture in a bioreactor (104, 106) from a reference state of a cell culture in a reference bioreactor (102). The bioreactor comprises the same medium (M1) as the reference bioreactor. The system comprises: •—a storage medium (114) comprising: •a PACO-reference profile (116) indicative of a deviation of a CO2 off gas rate ($ACO_R$-M-$_{ti}$) measured in the reference bioreactor from a predicted CO2 off gas rate ($ACO_{R\text{-}EXP\text{-}ti}$) of the reference bioreactor; •a data object comprising a medium-specific relation (136) between the pH value of the medium (M1) and a respective fraction of CO2 gas in a gas volume when said medium is in pH-CO2 equilibrium state with said gas volume and lacks the cell culture; •—an interface (128) for receiving (212) a current CO2 off gas rate ($ACO_{Bi}$-M-ti, $ACO_{B2}$-M-$_t$ i) and a current pH value ($pH_{Bi\text{-}ti}$) of the medium of the bioreactor (104, 106); •—a comparison unit (130) configured for computing (214, 216): •a PACO value ($PACO_{B1\text{-}tir}$ $PACO_{Bi\text{-}ti}$) the PACO-value being indicative of a deviation of a CO2 off gas rate ($ACO_{Bi}$-M-ti, $ACO_{B2}$-M-$_{ti}$) measured in the bioreactor from a predicted CO2 off gas rate ($ACO_{B1\text{-}EXP}$-ti, $ACO_{B2\text{-}E}$ xp-$_t$ i). a difference between the computed PACO value ($PACO_{Bi\text{-}ti}$, $PACO_{B2\text{-}ti}$) and a respective reference PACO value ($PACO_{R\text{-}ti}$) in the PACO-reference profile (116).

18 Claims, 8 Drawing Sheets

PACO profile for project: CHO cells in M1, 18 d

MONITORING STATE DEVIATIONS IN BIOREACTORS

CROSS-REFERENCE TO RELATED APPLICATIONS

This application is a U.S. National Stage entry of International Application No. PCT/EP2016/076167 filed Oct. 28, 2016, which claims the benefit of European Patent Application No. 15192387.7, filed Oct. 30, 2015, each of which is herein incorporated by reference in its entirety for all purposes.

FIELD OF THE INVENTION

The present invention relates to the field of biochemical engineering, and more particular to a system for monitoring bioreactors.

BACKGROUND AND RELATED ART

Bioreactors are commonly used for carrying out chemical processes, in particular processes performed by living organisms, in a controlled manner, e.g. in order to obtain a chemical compound, e.g. a particular peptide, protein, or other kind of chemical substance. A common goal is to operate the bioreactor in a way that the microorganisms or cells are able to perform their desired function with limited production of impurities and/or in a time- and cost-efficient manner. The environmental conditions inside the bioreactor, such as temperature, nutrient concentrations, pH, and dissolved gases, but also parameters of the cultivated cells and parameters of the bioreactor, such as its shape and size, affect the growth and productivity of the organisms. Thus, the growth and productivity of the organisms depend on a plurality of parameters which often influence each other. Thus, keeping all parameters constant in order to provide defined conditions for cultivating cells in a bioreactor is often a highly difficult task. Moreover, the complex interdependence of the plurality of parameters that have an impact on the growth and metabolism of a cell culture in a bioreactor is an obstacle for exactly reproducing the physico-chemical environment in a reference bioreactor in another bioreactor.

For example, WO2007/085880 A1 describes a method for on-line prediction of future performance of a fermentation unit using a plurality of parameters like concentration of product, biomass, sugar in the broth of batch/fed-batch fermentation unit containing bacteria and nutrients, whereby a computer model predicts the future product concentration based on current plant data. Every few hours a broth sample is taken and analyzed in the laboratory for biomass yield.

However, it is often not possible to operate a particular bioreactor with exactly the same parameters that were used for operating a reference bioreactor, and in this case, a comparison of the state of the cell culture in said particular bioreactor with a "desired" state of a reference cell culture in a reference bioreactor is difficult or error prone or even impossible.

SUMMARY

It is an objective of the present invention to provide for an improved system and method for monitoring a bioreactor as specified in the independent claims. Embodiments of the invention are given in the dependent claims. Embodiments of the present invention can be freely combined with each other if they are not mutually exclusive.

A "bioreactor" as used herein is a vessel in which a chemical process is carried out which involves organisms or biochemically active substances derived from such organisms. This process can be, for example, aerobic or anaerobic. A plurality of different bioreactor types exist which vary in shape (e.g. cylindrical or other), size (e.g., milliliters, liters to cubic meters) and material (stainless steel, glass, plastic, etc). According to embodiments, the bioreactor is adapted for growing cells or tissue in cell cultures. Depending on the embodiment and/or on the mode of operation, a bioreactor may be a batch bioreactor, fed batch bioreactor or continuous bioreactor (e.g. a continuous stirred-tank reactor model). An example of a continuous bioreactor is the chemostat.

In one aspect, the invention relates to a system for monitoring deviations of a state of a cell culture in a bioreactor from a reference state of a cell culture in a reference bioreactor. The bioreactor comprises the same medium as the reference bioreactor. The system comprises:
a storage medium comprising:
  a PACO-reference profile, the PACO-reference profile being a representation of the variation in a reference PACO value versus time, the PACO-reference profile being indicative of a deviation of a $CO_2$ off gas rate measured in the reference bioreactor from a predicted $CO_2$ off gas rate of the reference bioreactor, the predicted $CO_2$ off gas rate being the predicted off gas rate of said medium in pH-$CO_2$ equilibrium state in the reference bioreactor under absence of the cell culture and under the condition that the pH value of the medium in equilibrium state is identical to the pH value of the reference bioreactor measured when measuring the $CO_2$ off gas rate in the reference bioreactor, the PACO reference profile depending on the amount of $CO_2$ off gas produced by the cells of the cell culture in the reference bioreactor while cultivating the cell culture;
  a data object comprising a medium-specific relation, the medium-specific relation being specific for the medium and indicating a relation between the pH value of the medium and a respective fraction of $CO_2$ gas in a gas volume when said medium is in pH-$CO_2$ equilibrium state with said gas volume and lacks the cell culture;
an interface for repeatedly receiving, at a current time, a current $CO_2$ off gas rate of the bioreactor and a current pH value of the medium of the bioreactor measured during the cultivation of the cell culture in the bioreactor;
a comparison unit configured for computing, for each of the received current $CO_2$ off gas rates:
  a PACO value, the PACO-value being indicative of a deviation of a $CO_2$ off gas rate measured in the bioreactor from a predicted $CO_2$ off gas rate of the bioreactor, the predicted $CO_2$ off gas rate being the predicted off gas rate of said medium in the bioreactor in pH-$CO_2$ equilibrium state under absence of the cell culture and under the condition that the pH value of the medium in equilibrium state is identical to the pH value of the bioreactor measured when measuring the $CO_2$ off gas rate in the bioreactor, the PACO value depending on the amount of $CO_2$ off gas produced by the cells of the cell culture in the bioreactor while cultivating the cell culture, the computation of the PACO value using as input:
    the received current $CO_2$ off gas rate;

the received current pH value;
the total gas inflow rate of the bioreactor at the time of receiving the current CO2 off gas rate; and
the medium-specific relation;
in embodiments according to which the medium volume of the bioreactor differs from the medium volume of the reference bioreactor, the weight or volume of the medium or cell suspension in the bioreactor may in addition be used as input parameter as a normalization factor (for calculating a normalized PACO ("NPACO") value);
a difference between the computed PACO value and a respective reference PACO value in the PACO-reference profile.

The comparison unit is configured for outputting the computed difference, the computed difference being indicative of a deviation of the state of the cell culture in the bioreactor from the reference state.

Said features may be advantageous for multiple reasons:

The PACO value incorporates the "knowledge" of the deviation of a CO2 off gas rate measured (concurrently or in the past) in a reference bioreactor at a particular pH value from a CO2 off gas rate that is expected (predicted) for the reference bioreactor comprising said particular medium, whereby the prediction assumes the medium in the reference bioreactor is in pH-CO2 equilibrium and does not comprise the cell culture or any other factor that could have an impact on the pH-CO2 equilibrium of said medium.

Thus, the PACO value is an "integrative" parameter value that reflects any shift of a measured CO2 off gas rate from an expected ("predicted") CO2 off gas rate caused by any factor that has a causative effect on the pH-CO2 equilibrium of said medium. A PACO value does not discriminate if said causative effect relates to the cell metabolism and/or a modification of temperature or pressure and/or by increasing or decreasing the influx of fluids or gases that have an impact on the pH-CO2 equilibrium state. Thus, the PACO value may abstract away from the effect of many individual parameters having an impact on the cultivation condition of a cell culture and thus also having an impact on the state of the pH-CO2 equilibrium and on the CO2 concentration in the gas volume and off gas of a bioreactor. At a given pH value, the PACO typically rises in case of increased aerobic cell metabolism and/or growth of a cell culture under aerobic conditions. If the pH of the medium significantly decreases, the PACO typically decreases. Such a situation may happen as a result of cell metabolism, e.g. if CO2 generation of cells as well as secreted metabolites like lactate overcompensate CO2 removal from the bioreactor via the outgas lines and pipes.

Thus, the PACO value may more accurately reflect the "overall system state" of a bioreactor that has an impact on the growth condition of a cell culture than a set of multiple parameter values (temperature, pressure, CO2 pressure, pH value measured individually). Thus, it was observed that the PACO value can be used as a more accurate indicator of the state of a bioreactor and/or of the state of a cell culture in the bioreactor than a set of multiple bioreactor parameters considered concurrently but individually.

The PACO value may ease and improve a task of comparing the state of a bioreactor or a cell culture in said bioreactor with a ("desired") state of a reference cell culture in a reference bioreactor and thus may allow to compare the states of two cell cultures even in cases when one or more of the parameters having an impact on the cell growth, e.g. the size, dimension and/or stirring mechanism of the two compared bioreactors, significantly differ. Thus, PACO reference profiles may be obtained by monitoring a reference bioreactor under control parameters "known" to provide very good or optimal conditions for cultivating a particular cell culture for a particular purpose (peptide or protein isolation, etc). This profile may be used as PACO reference profile and thus as a kind of standard or "goal" for a particular type of cell culture project. When trying to cultivate the cell culture for the same purpose or "project" (e.g. obtaining a large amount of the same substance that was obtained in the reference bioreactor) in another bioreactor, the PACO value in said other bioreactor is repeatedly calculated to allow an accurate comparison of the cell culture state of said other bioreactor with the cell culture state in the reference bioreactor at a corresponding point in time (e.g. one hour, 5 hours, 10 hours after inoculation of the bioreactor with the cell culture or at each current moment in time in case the bioreactor and the reference bioreactor are operated in parallel and approximately synchronously). To operate the bioreactor and the reference bioreactor approximately synchronously may imply that the reference PACO values of the reference PACO profile are received continuously from the reference bioreactor, and each currently determined PACO value of the bioreactor is compared against the most current reference PACO value. By continuously comparing the current PACO values and current reference PACO values and by controlling the operation of the bioreactor value in a way that the PACO difference is minimized, an approximately synchronous operation of the bioreactor and the reference bioreactor may be achievable.

This comparison approach is much more accurate than the comparison of multiple parameters (temperature, pH, cell density in the medium, CO2 off gas rate, etc) individually, because typically, said parameters will not be completely identical. In particular, in case one or more of said parameters are determined by means of offline-measurements (commonly used in many bioreactor types), said measurements are often flawed by measurement errors resulting e.g. from temperature differences in the sample where the measurement is performed compared with the temperature in the medium of the bioreactors. In addition, the delay caused by the sampling process before determining said parameter values in the sample may prohibit an immediate action against any deviation of a state parameter of the bioreactor from a reference parameter value.

As the individual differences of the parameters in the monitored bioreactor from respective parameters in the reference bioreactor may mutually reinforce each other or may level each other out, depending on the concrete situation, an individual comparison of parameters of the monitored bioreactor with parameters of the reference bioreactor are much less accurate as they do now provide any insight on how said parameters influence each other. For example, an increased temperature may decrease solubility of CO2 in the medium and thus may increase the CO2 off gas rate, but may also increase the cell growth and thus result in an increased amount of CO2 generated by the cells. Decreasing temperature also increases the pH, which again has an impact on the PACO (directly or by triggering a response of a controller that counter-acts the decreased pH value e.g. by increasing CO2 influx rate). The (temperature-dependent) metabolism of the cells may, again, have an effect on the pH of the medium, e.g. by excreting basic or acidic substances such as lactate. The pH value of the medium, again, may have an impact on the amount of CO2 dissolved in the medium. A PACO value, however, integrates the mutual dependencies of the parameters having an impact on the pH-CO2 equilibrium of the medium and incorporates information on the impact of the pH value of said medium on the pH-$CO_2$ equilibrium of said medium.

Applicant has surprisingly observed that a minimum input data set comprising only the current $CO_2$ off gas rate, the current pH value, the total gas inflow rate of the bioreactor at the time of receiving the current $CO_2$ off gas rate and the medium-specific relation are sufficient for accurately comparing the states of two bioreactors and respective cell cultures. As all said input data values can be obtained in the form of online measurement values, it is not necessary any more to take samples for comparing the state (which may result in a contamination of the bioreactor or in the generation of measurement values which are inaccurate due to sampling effects like temperature loss, pH change in the sample due to gas exchange with the environmental air, etc.).

In a further beneficial aspect, embodiments of the invention allow comparing the states of cell cultures cultivated in bioreactors having different dimension or shape. Thus, the PACO reference profile may also be used for scaling up or scaling down a biochemical process that was optimized or examined in a reference bioreactor to a bioreactor having different size and dimension.

In a further aspect, using $CO_2$ off gas rates as input for calculating a current PACO value may be beneficial, because $CO_2$ off gas meters ("$CO_2$ off gas analyzers") are non-invasive, do not need a sampling, can be easily obtained in real time and deliver a value, the $CO_2$ off gas rate (or a $CO_2$ concentration in the off gas from which the $CO_2$ off gas rate can be derived), which may integrate cell specific parameters ($CO_2$ emitted by cells) and engineering parameters (total gas influx rate, current pH, pressure, temperature, stirring rate, stirring configuration, bubble size and distribution, etc.). Thus, $CO_2$ off gas analyzers may give immediate response to intended or unintended process changes (in contrast to e.g. cell densities or cell counts).

Thus, calculating a PACO value for a reference reactor for generating a PACO reference profile and comparing dynamically obtained PACO values of a monitored and/or controlled bioreactor with respective reference PACO values allows to identify if the conditions in the monitored bioreactor constitute a largely similar or identical "environment" for cultivating cells like the environment provided by the reference bioreactor.

In many bioreactor types, the influx gasses are fed (as a gas mixture or via separate openings) into the bioreactor via one or more submersed gas intakes. In case the bioreactor comprises an additional headspace aeration, the influx rate of said "headspace" influx gas fraction and/or the air circulation of the gas phase above the medium have to be configured such that all gases fed into the bioreactor via headspace aeration reach pH-$CO_2$ equilibrium with the medium of the bioreactor before leaving the bioreactor. Also in case the headspace aeration is the only aeration mechanism of the bioreactor, the influx rate of said "headspace" influx gas fraction has to be configured such that all gases fed into the bioreactor reach pH-$CO_2$ equilibrium with the medium of the bioreactor before leaving the bioreactor.

Alternatively (e.g. in case a pH-$CO_2$ equilibrium of the headspace aeration gases with the medium cannot be reached in time), the additional headspace aeration is turned off before measuring the $CO_2$ off gas rate in a bioreactor. This may allow avoiding computing an erroneous PACO value caused by the additional headspace aeration which may result in a $CO_2$ off gas concentration that differs from the current pH-$CO_2$ equilibrium $CO_2$ concentration of the medium.

According to embodiments, the temperature and pressure of the reference bioreactor and of each bioreactor monitored and/or controlled by using the PACO reference profile obtained from said reference bioreactor is identical to the pressure and temperature of the medium used for empirically determining the medium-specific relation at least at the time when inoculating the reference bioreactor or the bioreactor with the cell culture. At a later stage of the cultivation of a cell culture, the temperature and/or pressure of the monitored and/or controlled bioreactor(s) may differ from the temperature and/or pressure used during inoculation and may even differ from the temperature and/or pressure of the reference bioreactor at a corresponding time point in the reference PACO profile.

According to embodiments, the received current $CO_2$ off gas rate, the received current pH value, the total gas inflow rate of the bioreactor at a particular time ti (t0, t1, . . . , tmax) and the medium-specific relation are the only input parameters for calculating the PACO values for the monitored bioreactor. In embodiments where the medium volume of the reference bioreactor differs from the medium volume of the monitored and/or controlled bioreactor, the volume or mass of the medium in the bioreactor may be used in addition as input for calculating the PACO values of the bioreactor. In this case, the calculation of the reference PACO profile comprises using the volume or mass of the medium in the reference bioreactor in addition as input for calculating the reference PACO values of the reference bioreactor. The parameter "i" may represent a predefined number of minutes or hours lapsed since inoculation or since a predefined time interval before inoculation. For example, the current pH value may be used as input for the medium-specific relation to calculate an expected fraction of $CO_2$ in the off gas of the monitored bioreactor at said pH value under the assumption that the medium in the bioreactor is in pH-$CO_2$ equilibrium state with the gas volume above the medium and does not comprise any cells or other factors having an impact on the pH-$CO_2$ equilibrium. The calculated $CO_2$ volume fraction of the $CO_2$ off gas of the bioreactor correlates with the $CO_2$ partial pressure of the gas volume above the medium in the bioreactor, whereby the $CO_2$ partial pressure depends on the pH value in the medium and can be characterized by a pH-$CO_2$ chemical equilibrium according to the Henderson-Hasselbalch equation. The calculated predicted/expected $CO_2$ volume fraction and the measured total gas inflow rate (which is identical to the total outgas rate) may be used for calculating an expected $CO_2$ outgas rate for the bioreactor.

The pH value and $CO_2$ volume fraction ("$CO_2$ concentration") in the off gas can easily be measured without taking any sample from the medium comprising the cell culture and thus without risking the bioreactor becomes infected by undesired fungi and bacteria. In addition, contrary to offline-pH measurements in samples of the bioreactor, measuring the $CO_2$ volume fraction in the off gas is an online-measurement. Thus, any time offset effects caused by the time needed for the sampling process until a measurement value can be determined can be avoided. Offset effects in offline measurements may reduce the accuracy of controlling the state of the controlled bioreactor in a manner that it closely follows a state profile of the reference bioreactor. The total gas influx rate is basically identical to the total off gas rate of a bioreactor and is predefined or can easily be determined and used in combination with the measured $CO_2$ volume fraction in the off gas to determine the currently measured $CO_2$ off gas rate.

In a further beneficial aspect, many current bioreactor systems already comprise or can easily be coupled with sensors for CO2 concentration in the off gas and/or for the current CO2 off gas rate, the total gas inflow rate and/or a current pH value in the medium of the bioreactor. Thus, the approach can easily be implemented in a variety of existing bioreactors and bioreactor monitoring and/or control frameworks without having to install additional sensors or other hardware modules.

In a further beneficial aspect, the PACO value provides an immediate indication of changes in the biochemical milieu of a bioreactor. This is not the case with cell counts, particle measurements, metabolite measurements and all kinds of offline measurements (i.e., measurements performed on a sample of the medium of the bioreactor extracted from the bioreactor in production mode). By using a PACO value that is a derivative of a medium-specific relation, a currently measured CO2 off gas rate and a currently measured pH value, bioreactor comparability can be achieved despite probe drifts (changing amounts of dissolved CO2 in the medium, changes in the pH value of the medium). In addition, superior plausibility checks can be performed.

A further beneficial aspect of using CO2 off gas rate as input is that off gas analyzers can be calibrated anytime and do not have to be autoclaved.

In a further beneficial aspect, the PACO value is calculated specifically for the medium used in the bioreactor (and that is or was used in the reference bioreactor), and therefore incorporates knowledge on the correlation between pH and off gas carbon dioxide. That means that PACO is not only influenced by changing pH, but also by the typical CO2 off gas rate of said medium at a particular pH value. That makes PACO perfectly suitable to not only address CO2 outgas differences caused by the bioreactor configuration, but also caused by changes in the pH value of the medium.

In a further beneficial aspect, the PACO value can be used for comparing the states of different bioreactors with all aeration modes (both variable and constant) and/or in situations when the temperature or pressure of the monitored bioreactor differs from the temperature and/or pressure of the reference bioreactor.

According to embodiments, a control module of the bioreactor modifies the pH value in the bioreactor solely by modifying the CO2 influx rate. This may have the advantage that the composition of the medium is not modified by any additional acidic or basic substances (only the concentration of the solved CO2 and its dissociation products will vary with varying CO2 gas concentration).

According to embodiments, the method comprises controlling the pH value of the medium in the bioreactor in a way that the pH value remains within a predefined range of allowed pH values, also referred to as "pH deadband". For example, the range of allowed pH values may be [6.8-7.2] in some embodiments, or [6.95-7.05] in other embodiments. In case the pH value of the medium is below the lowest allowed pH value or is above the highest allowed pH value, the controller of the bioreactor—irrespective of the current PACO value of the bioreactor—takes appropriate actions to shift the pH value in the medium into the allowed range, e.g. by modifying the amount of CO2 influx. As long as the pH value of the medium of the bioreactor is within the allowed pH range, the controller modifies the pH value solely in dependence of a determined deviation of a current PACO value from a corresponding reference PACO value.

This may have the advantage that a smoother and more fine grained control of the pH value in the medium of the bioreactor is achieved and the fluctuations of the pH value in the medium may be decreased compared to a purely "pH deadband"/threshold-based control of the pH value of a bioreactor.

According to embodiments, the medium-specific relation is an equation $FCO2_{M1}(pH)=REL-M1(pH)$ obtained by mathematically fitting multiple empirically determined pairs of a pH-value of a sample of the medium used in the bioreactor and in the reference bioreactor and a respectively measured fraction of CO2 gas in a gas volume above said sample. The sample may be, for example, the totality of a cell free medium in a bioreactor or a cell free aliquot of said medium.

$FCO2_{M1\text{-}EXP}(pH)$ is the predicted fraction of CO2 gas ("predicted CO2 concentration") in a gas volume of a sample of the medium when said medium has a given pH-value and is in pH-CO2 equilibrium state with said gas volume and lacks the cell culture. $FCO2_{M1\text{-}M}$ is the measured fraction of CO2 gas ("measured CO2 concentration") in a gas volume being in CO2-pH equilibrium state with a medium M1, e.g. in the off gas of a bioreactor comprising medium M1.

A "PACO value" value is a data value. As was specified above, the PACO-value is a data value that is indicative of a deviation of a CO2 off gas rate measured in the bioreactor from a predicted CO2 off gas rate of the bioreactor. The predicted CO2 off gas rate is the predicted off gas rate of said medium in the bioreactor in pH-CO2 equilibrium state under absence of the cell culture and under the condition that the pH value of the medium in equilibrium state is identical to the pH value of the bioreactor measured when measuring the CO2 off gas rate in the bioreactor. The PACO value depends on the amount of CO2 off gas produced by the cells of the cell culture in the bioreactor while cultivating the cell culture. The computation of the PACO value uses as input preferentially solely the following data: the current CO2 off gas rate and the current pH value and total gas inflow rate of the bioreactor at the time of receiving (measuring) the current CO2 off gas rate. In addition, a medium-specific relation is used as input.

According to embodiments, the system used for monitoring and/or comparing bioreactor states is configured for computing the PACO value ("$PACO_{B1\text{-}ti}$", "$PACO_{B2\text{-}ti}$"). The computation of the PACO value comprises inputting the received current pH value into the medium-specific-relation for obtaining a predicted CO2 concentration ("$FCO2_{EXP}$", e.g. $FCO2_{M1\text{-}M}$ for bioreactor B1 or $FCO2_{M2\text{-}M}$ for bioreactor B2) in the gas volume of the bioreactor in equilibrium state with the medium at the time of measuring the current CO2 off gas rate and the current pH value;

multiplying the predicted CO2 concentration ("$FCO2_{EXP}$") with the total gas inflow rate of the bioreactor for obtaining the predicted CO2 off gas rate ("$ACO_{EXP}$") of the bioreactor; the predicted CO2 off gas rate is the predicted off gas rate of said medium actor in pH-CO2 equilibrium state under absence of the cell culture and under the condition that the pH value of the medium in equilibrium state is identical to the received, measured current pH value of the bioreactor input into the medium-specific relation;

subtracting the measured CO2 off gas rate ($ACO_{B1\text{-}M\text{-}ti}$, $ACO_{B2\text{-}M\text{-}ti}$) of the bioreactor from the predicted CO2 off gas rate ("$ACO_{MEASURED}$", e.g. $ACO_{B1\text{-}EXP\text{-}ti}$, $ACO_{B2\text{-}EXP\text{-}ti}$) of the bioreactor for obtaining the PACO value as the difference of the measured and the expected CO2 offgas rate.

The PACO value depends on the amount of CO2 off gas produced by the cells of the cell culture in the bioreactor while cultivating the cell culture and represents an "integrative" parameter hat also depends on the current pH value and empirically derived knowledge on the interdependence between pH and the equilibrium CO2 concentration of the particular medium used.

According to embodiments, the computation of the predicted CO2 off gas rate $ACO_{B1-EXP-ti}$ of the bioreactor B1 at the current time (ti) is performed according to:

$$ACO_{B1-EXP-ti}[mol/min] = \left(\frac{FCO2_{B1-EXP-ti}[\%]}{100}\right) \times TGI_{B1}\left[\frac{mol}{min}\right],$$

wherein the $TGI_{B1}$ is the total amount of gas influx of the bioreactor B1 at the current time (ti), and wherein $FCO2_{B1-EXP-ti}$ is the predicted CO2 concentration in the gas volume of the bioreactor in % in equilibrium state with the medium at the time of measuring the current CO2 off gas rate and the current pH value.

The above mentioned computation of the PACO value may, in some embodiments, assume the relationship between a mol of CO2 and its volume to be that of an ideal gas. Other embodiments may in addition comprise additional computation steps for compensating effects of the temperature and/or pressure of the currently monitored bioreactor on the mol volume of CO2, for compensating for measurement errors, humidity and/or other potential sources of error.

According to embodiments, the above mentioned computation steps are performed analogously for the reference bioreactor for computing the reference PACO values and for generating the reference PACO profile.

A "medium-specific relation" as used herein is a function, e.g. an equation, which predicts a CO2 concentration in a gas volume that is in pH-CO2 equilibrium state with a particular (cell-free) medium, the medium having a given pH-value. The function is obtained empirically for said particular medium and is adapted to predict the CO2 off gas rates for many different pH values provided as input.

A "medium", also referred to as "growth medium" or "culture medium" is a liquid designed to support the growth of microorganisms or cells. There are different types of media for growing different types of cells. There are media used for cell culture, which use specific cell types derived from plants or animals, and for microbiological culture, which are used for growing microorganisms, such as bacteria or fungi. Some organisms require specialized environments due to complex nutritional requirements. For example, the medium can consist of water comprising sodium bicarbonate or calcium carbonate that is basically free of any further components. Likewise, the medium can be a "rich medium" comprising additional components like nutrients, growth factors, hormones or other proteins, etc. For example, the medium can be a nutrient medium, a minimal medium, a differential medium, or an enriched medium.

A "FCO2 value" is a data value. An "ACO value" is a data value. The meaning and calculation of the respective data values are described herein for various embodiments of the invention. "FCO2" or "CO2 [%]", also referred to as "CO2 concentration" is the "fraction CO2 gas" in a gas volume, e.g. In the off gas of a bioreactor.

A "profile" is a set of data values or a mathematical relation that indicates the variation of a parameter value over time. The parameter value can be, for example, a PACO value, a CO2 concentration in the off gas ("fraction CO2" or "FCO2"), a CO2 off gas rate ("ACO value") or the pH value obtained from a bioreactor.

The prediction of the ACO value is specific for the medium used in the reference bioreactor and in the bioreactor compared with the reference bioreactor.

The "pH" value is an input parameter value used to specify a pH value of the medium M1 in ph-CO2 equilibrium state under the absence of the cell culture.

"REL-M1" is a set of one or more parameters connected by operators.

The parameters are obtained by:
adjusting samples of the medium lacking the cell culture, to multiple different pH values, thereby letting the samples reach pH-CO2 equilibrium with the gas volume,
determining the fraction of CO2 gas in a respective gas volume being in ph-CO2 equilibrium with the medium in the samples,
plotting the determined CO2 gas fractions against the respective equilibrium pH values of the samples,
fitting a curve in the plotted values and
deriving the parameters of the medium-specific relation from the fitted curve.

Thus, the medium-specific relation may be identified empirically, e.g. before the reference bioreactor is inoculated with the reference cell culture. According to embodiments, it is also possible to empirically determine the medium specific relation after the cell culture was cultivated and grown in the reference bioreactor. In this case, however, it is necessary that the pH value, total gas influx rate and CO2 fraction in the off gas of the reference bioreactor were monitored and stored in order to allow to calculate the PACO reference profile for said reference bioreactor as soon as the medium-specific relation is empirically determined.

According to some embodiments, the medium specific relation is obtained by filling a bioreactor, e.g. the reference bioreactor, with the medium, whereby the medium does not comprise the cell culture cells, and setting the temperature and pressure of the reference bioreactor to predefined values, e.g. 20° C. and standard atmospheric pressure. Then, the medium may be set to different pH values e.g. by increasing or decreasing the CO2 concentration in the gas volume above the medium via a modified CO2 gas influx rate, and after some time (typically minutes or hours) when the medium has equilibrated (reached pH-CO2 equilibrium state at the given pH and the predefined temperature and pressure), the CO2 concentration in the gas volume above said medium (which correlates with the CO2 partial pressure at said equilibrium state) is measured. Said measuring is performed e.g. by analyzing the CO2 concentration in the gas volume above the medium or via the CO2 volume fraction in the off gas. The acquired pairs of equilibrium pH-values and CO2 concentrations (or CO2 off gas values) measured in the sample (bioreactor or aliquot) are plotted, i.e., represented in a coordinate system. The plotting may be performed automatically by a computer system which may in addition output the plot in the form of a paper-based printout and/or a plot displayed on a computer screen. The plotting may also be performed manually. A curve is fitted automatically or manually to said plot and parameters being descriptive of said fitted curve are computed. The parameters define the medium-specific relation of pH-value and CO2 concentration of a gas volume above said medium when said medium is in pH-CO2 equilibrium at a particular pH value. After having computed the parameters, the medium in the reference bioreactor can be set to a desired pH value, can be inoculated with the cell culture and can be monitored (in respect to a current pH value in the medium, a current CO2 off gas rate and current total gas influx rate) for obtaining the PACO reference profile. This approach has the advantage that no extra-equipment for the empirical determination of the medium-specific relation is possible and that the medium can be used for obtaining said relation and for growing the cells.

According to other embodiments, the medium-specific relation is obtained by creating multiple samples in the form of aliquots of said medium, each sample having a different pH value. The samples are left at a predefined temperature and pressure for some time (e.g. several minutes or hours) to allow pH-CO2 equilibration between the gas and the liquid medium in each sample.

The samples can be obtained sequentially, e.g. by changing the pH value of a single sample and performing sequential measurements, or can be obtained by creating multiple samples of said medium in parallel, each aliquot being set to a different pH value by modifying the CO2 concentration of the gas volume above the medium. The sample can be filled into any container allowing the setting and measuring of a current pH value and allowing the modification of the CO2 concentration and the measuring of a CO2 concentration or CO2 off gas rate at equilibrium state.

According to some embodiments, the equation $FCO2_{M1}(pH)=REL-M1(pH)$ is a linear equation according to $FCO2_{M1}(pH)[\%]=a1 \times pH+a2$. In this case, the parameters a1 and a2 are the parameters derived from the fitted curve. The unit [%] relates to the CO2 gas fraction of the gas volume above the medium in a sample at pH-CO2 equilibrium state.

According to other embodiments, the equation $FCO2_{M1}(pH)=REL-M1(pH)$ is a polynomial equation according to $FCO2_{M1}(pH)[\%]=b1 \times pH^2+b2 \times pH+b3$. In this case, the parameters b1, b2 and b3 are the parameters derived from the fitted curve.

Empirically determining the medium-specific relation and the corresponding medium-specific parameters may have the beneficial effect that even in case the exact composition of the medium is not known (which is commonly the case for many media in the market), the impact of a particular pH value on the equilibrium CO2 concentration in an air volume in pH-CO2 equilibrium with said medium can be determined experimentally. Thus, the PACO value can be calculated also when using media whose composition is not known.

According to preferred embodiments, the cell culture of the bioreactor comprises the same or a very similar type of cells like the cell culture cultivated in the reference bioreactor. The metabolism and the growth profiles of different cell types, e.g. bacteria and yeast, are usually not comparable. For example, the cells can be eukaryotic cells, e.g. yeast cells, plant cells, or mammalian cells, in particular human cells. According to other embodiments, the cells can be bacteria or archaea cells.

According to embodiments, in case the computed difference between the computed PACO value and a respective reference PACO value in the PACO-reference profile exceeds a threshold value, the outputting of the computed difference comprises automatically outputting an alarm signal. The alarm signal can be, for example, an acoustic and/or optic signal, a message communicated to a user device (e.g. a computer or mobile phone) or an automated bioreactor control unit. The message may be communicated via a network, e.g. the Internet or an intranet.

Said features may allow a user to manually take actions in order to modify parameters of the bioreactor or the medium contained therein such that the difference to the reference PACO value is minimized and/or may allow an automated control unit to automatically perform actions which are expected to reduce the difference in the compared PACO value.

According to embodiments, the medium used in the reference bioreactor and in the monitored and/or controlled bioreactor is a carbonate-buffered medium.

In its broadest sense, any solution capable of dissolving at least a small amount of CO2 is a carbonate-buffered medium, as the solved CO2 will dissociate into HCO3− and H+ ions according to the following pH-CO2 equilibrium equation: $CO_2+H_2O \rightarrow HCO_3^- +H^+$.

According to embodiments, a "carbonate buffered medium" is a medium comprising at least 10 mMol of a carbonate-salt per liter medium, whereby the medium is a cell free medium (the metabolism of cells may modify the pH value and thus the amount of carbonate salt in the medium). The carbonate salt can be, for example, sodium bicarbonate or calcium carbonate.

Using a buffered medium has the advantage of reducing pH fluctuations in particular in the biological pH range of 6-8.

Carbonate buffers have the disadvantage that the pH value at pH-CO2 equilibrium depends on the carbon dioxide partial pressure in the air and on the CO amounts generated in the medium later by the cells, and CO2 has a limited solubility. Thus, the use of carbonate buffers in bioreactors according to state of the art approaches often prohibited an accurate comparison of the states of cell cultures cultivated in bioreactors comprising a carbonate buffered medium at different temperature and/or pressure conditions. Using a carbonate buffered medium in combination with the PACO-based state comparison of bioreactors has the beneficial effect that it is possible to use a medium whose buffer does not interfere with the cell metabolism as strongly as, for example, phosphate buffers, but which nevertheless allows comparing bioreactors which operate at different temperatures and/or pressures. Even in case the carbonate salt of the buffer interferes with the cell metabolism, the PACO value integrates said effect and still allows for an accurate comparison and/or synchronization of bioreactor states.

According to embodiments, the reference bioreactor differs from the bioreactor in respect to one or more of the following features:

a) the gas volume in the bioreactor,
b) the medium volume in the bioreactor,
c) the Reynolds number of the bioreactor,
d) the Newton number of the bioreactor,
e) the dimensions of the bioreactor (e.g. height to diameter ratio),
f) geometrical features of the bioreactor and/or bioreactor baffles (e.g. the cylindrical or polygonal shape of a bioreactor, the size, shape, orientation and position of baffles and other components within the bioreactor such as sensors, pumps, stirrers, etc.),
g) the stirrer configuration (e.g. the size, orientation and shape of a stirrer in the bioreactor, the stirring intervals, the duration of the stirring interval, the number and relative orientation of the stirring units),
h) the stirring rate,
i) the volumetric mass transfer coefficient for oxygen (kLa) of the bioreactor,
j) total gas influx rate and/or O2 influx rate and/or N2 influx rate and/or CO2 influx rate, k) power input,
l) pressure in the bioreactor,
m) gas bubble hold time in the medium,
n) gas bubble size and distribution in the medium,
o) surface speed (may be expressed in meters per second [m/s] and may represent the relative speed between a shaft and a bearing of the medium in a bioreactor),
p) a parameter calculated as a derivative from one or more of the parameters a)-o).

The "power input" parameter as used herein specifies the amount of power input of a stirrer of a bioreactor. Different stirrer configurations can have different power inputs at identical agitation or identical tip speeds. Power input at identical stirrer speeds may depend on the viscosity of the medium.

Thus, embodiments of the invention may allow to compare the state of a bioreactor with the state of another ("reference") bioreactor even in case the two compared bioreactors differ in respect to many different engineering parameters. This may be highly advantageous as it has been observed that keeping all said parameters identical to allow a comparison and/or control of bioreactor states was often not feasible in practice. By using a PACO value, the state of two bioreactors can be easily compared (identical PACO value means identical state regarding relevant parameters) even in case the two bioreactors have different Reynolds and/or Newton numbers, have a different speed or configuration of the stirrer or the like.

According to embodiments, the monitored and/or controlled bioreactor is operated by using the aeration rate as a control parameter for counteracting deviations of the current PACO value of the bioreactor from a reference PACO value.

Surprisingly, it was observed that in case the aeration rate is used as control parameter to counteract any deviation of a PACO value from a desired reference PACO value, the PACO value allows to compare the states of bioreactors also in case pressure differences (in the range that is typically encountered when operating bioreactors, e.g. pressure variations caused by weather-induced changes in the atmospheric pressure) exist between the two bioreactors. In general, the pressure has an impact on the pH-CO2 equilibrium of a medium. A rising pressure results in a reduction of the CO2 off gas rate while the pH value remains constant. In effect, the PACO value decreases in case the pressure rises. To compensate the effect of the rising pressure, a controller unit is used, according to embodiments, that automatically reduces the aeration rate (measured e.g. in vvm=gas volume flow per unit of liquid medium volume per minute) until the PACO difference is identical to a desired reference PACO value or has reached zero or has reached a predefined minimum aeration rate (to ensure the cells are supplemented with a sufficient amount of oxygen). By reducing the aeration rate, also the CO2 off gas rate is reduced and the PACO increases. Thus, by using the aeration rate as control parameter, pressure deviations can be easily compensated and the PACO can be used as reliable state indicator of a bioreactor and its cell culture.

According to some embodiments, the reference bioreactor and the bioreactor are located in different geographic regions, e.g. different buildings, cities or countries. In a beneficial aspect, the comparison of PACO values allows accurately comparing states of cell cultures cultivated (sequentially or in parallel) in bioreactors which differ in respect to one or more of the above mentioned parameters from each other. Thus, embodiments of the invention may allow grooving a cell culture in a bioreactor that has completely different dimensions as the reference bioreactor and may deviate from the reference bioreactor in many aspects.

Preferentially, the CO2 gas influx rates of the monitored and/or controlled bioreactor and the reference bioreactor at a respective time ti in the profile are identical to allow establishment of comparable dynamic pH-CO2 equilibria in both bioreactors.

In a further beneficial aspect, costs are reduced and the flexibility is increased: previously, in order to cultivate cells in a particular bioreactor at similar or identical conditions as were observed in a reference reactor, it was often necessary to ensure that the size, shape, stirring mechanism and a plurality of further features of the bioreactor were identical to the reference bioreactor in order to ensure that each individual parameter of the particular bioreactor is as similar to the reference bioreactor as possible. This increased costs because available bioreactors could not be used if their size, the bioreactor type and/or the version of said bioreactor or some of its parts were not identical to the respective features of the reference parameters. Often, different standards and norms for valves and other bioreactor elements exist in different countries. Thus, in several cases it is practically not possible to run a bioreactor whose dimensions and/or components are identical to the reference bioreactor, making a comparison of bioreactors of different countries difficult or impossible. By using a PACO reference value as described above, it was observed that differences in respect to size or shape or any other feature that has an impact on the pH-CO2 equilibrium of the medium and thus has an impact on the growth of the cells in said medium are leveled out and an accurate comparison of cell culture states is possible even in case the two compared bioreactors or their components differ significantly.

According to embodiments, the computation of the PACO value of the monitored and/or controlled bioreactor at a current time comprises computing, for each of the received current CO2 off gas rates and pH values of the monitored and/or controlled bioreactor:

the expected CO2 off gas fraction $FCO2_{B1\text{-}EXP\text{-}ti}$ of a current outgas volume of the bioreactor (104) according to: $FCO2_{B1\text{-}EXP\text{-}ti} = REL\text{-}M1\,(pH_{B1\text{-}ti})$, wherein $FCO2_{B1\text{-}EXP\text{-}ti}$ is a predicted CO2 off gas fraction of the total off gas volume ($TGO_{B1}$) of the bioreactor (104) in % at the current time (ti), the prediction being calculated by using the received current pH value ($pH_{B1\text{-}ti}$) as input for $REL\text{-}M1(pH_{B1\text{-}ti})$, wherein REL–M1 is the medium-specific relation (136) of the medium (M1), wherein $pH_{B1\text{-}ti}$ is the received current pH value in the medium of the bioreactor (104, 106) at a time ti; thus, the expected CO2 off gas fraction in the bioreactor is computed under the assumption that the medium of the bioreactor lacks the cell culture, has the pH value used as input of the medium-specific relation and is in pH-CO2 equilibrium state with the gas phase in the bioreactor above said medium and thus is also in equilibrium with the total off gas volume of said bioreactor.

an expected CO2 off gas rate $ACO_{B1\text{-}EXP\text{-}ti}$ [mol/min] value according to:

$$ACO_{B1\text{-}EXP\text{-}ti}[\text{mol/min}] = \left(\frac{FCO2_{B1\text{-}EXP\text{-}ti}}{100}\right) \times TGI_{B1},$$

wherein the $ACO_{B1\text{-}EXP\text{-}ti}$ value is the expected CO2 off gas rate of the bioreactor (104) when the medium of the bioreactor has the currently measured pH value and is in pH-CO2 equilibrium with the gas phase above said medium, wherein the $TGI_{B1}$ is the total amount of gas influx of the bioreactor (104) at the current time (ti); the total amount of gas influx of the bioreactor is approximately identical to the total amount of gas outflow;

the $PACO_{B1\text{-}ti}$ value according to: $PACO_{B1\text{-}ti} = ACO_{B1\text{-}EXP\text{-}ti} - ACO_{B1\text{-}M\text{-}ti}$, wherein $ACO_{B1\text{-}M\text{-}ti}$ is the CO2 off gas rate measured at time ti in the bioreactor.

According to embodiments, the medium in the reference bioreactor has a first volume and a first total mass. The medium in the monitored and/or controlled bioreactor has a second volume and a second total mass. The first volume and the second volume differ from each other. Accordingly, the first mass and the second mass differ from each other. The computation of the difference between each one of the computed PACO values and its respective reference PACO value in the PACO-reference profile comprises:

dividing, by the processor, the computed PACO value by the second volume; and dividing, by the processor, the respective reference PACO value in the PACO-reference profile by the first volume; or dividing, by the processor, the computed PACO value by the second mass; and dividing, by the processor, the respective reference PACO value in the PACO-reference profile by the first mass.

Said features may be advantageous as they allow comparing the state of a cell culture cultivated in bioreactors respectively comprising different volumes of the medium. For example, the reference bioreactor may be a test bioreactor comprising 100 liter of the medium. The reference bioreactor may be used for identifying suitable parameters (temperature, pressure, feeding rate, O2 influx rate, pH, stirring rate and the like) for efficiently cultivating a cell culture, e.g. for purifying a particular peptide. Thus, the reference reactor may have been used multiple times under different conditions to find out optimum parameters for cultivating the cells in the reference bioreactor. After having identified the "optimum" or "suited" set of parameters for the reference bioreactor, at least one cell culture is cultivated in the reference reactor under said "optimal" parameter set. The reference PACO profile is obtained from the reference reactor while cultivating the cell culture under said "optimal" or "suitable" conditions.

In "production mode" (which typically follows the test mode) the cell culture is cultivated on a large scale ("production mode") in a larger bioreactor or even in multiple, larger bioreactors operated in parallel. As the dimension and optionally also further parameters of the bioreactor like the steering configuration, O2 influx rate and/or other parameters of the larger bioreactor may differ from the reference bioreactor, using the PACO reference profile calculated in the above described, volume-dependent manner allows an accurate comparison of cell culture states even in case the cell cultures are cultivated in bioreactors of significantly different sizes. For example, some parameters like stirring rate, stirring configuration etc. may be specific to the reference bioreactor and may not be reproducible in another bioreactor in which the cell culture shall be grown in larger scale. According to a further example, the volume of the medium in the bioreactor used for production purposes may be 10 times, 100 times or even more than 1000 times larger than the volume of the medium in the reference bioreactor. Thus, embodiments of the invention allow accurately scaling up the cultivation of cell cultures over large scale differences. Analogously, embodiments of the invention allow scaling down the cultivation of cell cultures over large scale differences by normalizing the PACO value and the reference PACO value with the different media volumes or media masses.

According to embodiments, the PACO reference profile covers multiple phases of operating the reference bioreactor. The phases comprise:

a feed-free phase during which the cell culture is cultivated in the reference bioreactor without feeding;

a feeding phase during which the cell culture is cultivated in the reference bioreactor in the presence of a given feeding rate, the cell culture not excreting a metabolite affecting the pH value of the medium; a metabolite affecting the pH value could be, for example, lactate and/or H+ ions.

a feeding phase during which the cell culture is cultivated in the reference bioreactor in the presence of a given feeding rate, the cell culture excreting a metabolite affecting the pH value of the medium.

According to embodiments, the system comprises a control unit configured for automatically modifying one or more control parameters of the bioreactor thus that the difference between the computed PACO values and the respective reference PACO values in the PACO-reference profile is minimized.

Thus, embodiments of the invention may not only to monitor and compare the state of cell cultures cultivated in bioreactors with significantly different properties and parameters, but also allow to use this information to control the bioreactor in a manner that the conditions in the bioreactor that are relevant for cell growth are highly similar to the conditions in the reference bioreactor while obtaining the reference PACO profile.

The control unit may be, for example, a control computer being operatively coupled to the bioreactor that is controlled. Alternatively, the control unit may be a data processing device of a user, e.g. of an operator of the bioreactor, the data processing device having installed a bioreactor management software application that automatically or semi-automatically monitors and/or controls the bioreactor in a way that the difference between dynamically obtained PACO values of the bioreactor and the reference PACO values in the reference PACO profile are minimized. For example, the data processing system can be a desktop computer, a smart phone, a tabloid computer, or the like. The comparison unit may be a piece of automatically executable program logic, e.g. in the form of hardware, software and/or firmware logic. The comparison unit may be operatively coupled to the control unit, e.g. may be an integral part of the control unit or may be an application program configured to interoperate with the control unit.

According to embodiments, the control unit may control the bioreactor as follows:

In case the PACO values obtained in the monitored and/or controlled bioreactor are higher than the respective reference PACO values in the PACO reference profile, the control unit automatically modifies one or more control parameters of the bioreactor by performing one or more of the following operations:

reduce total air influx rate and/or reduce O2 gas influx rate and/or reduce the CO2 gas influx rate and/or reduce the base influx rate to the bioreactor and/or modify the pressure or the temperature of the bioreactor.

In case the PACO values are lower than the respective reference PACO values in the PACO reference profile, the control unit automatically modifies one or more control parameters of the bioreactor by performing one or more of the following operations:

increase the total air influx rate and/or increase the O2 gas influx rate and/or increase the CO2 gas influx rate and/or increase the base influx rate to the bioreactor and/or modify the pressure or the temperature of the bioreactor.

Using a PACO deviation as a control parameter in order e.g. to add acid or basic substances in order to modify the pH value of a medium instead of minimizing parameter differences individually (e.g. by minimizing pH-differences to a reference pH in the reference bioreactor) may have the advantage that the quality of control is improved: The PACO value depends on the pH value, but is not identical to the pH value. The pH value is thus, according to embodiments, indirectly controlled via the PACO-difference control parameter. This introduces a kind of robustness to the control loop which prohibits or at least reduces the well known problem of oscillation of the controlled parameter over a set point value due to controller latency.

According to embodiments, the system further comprises the controlled and/or monitored bioreactor. The system may optionally further comprise an additional bioreactor and the reference bioreactor, and/or a display device for displaying the difference of PACO profiles on a screen.

In a further aspect, the invention relates to a method for monitoring deviations of a state of a cell culture in a bioreactor, also referred herein as "monitored and/or controlled bioreactor", from a reference state of a cell culture in a reference bioreactor. The bioreactor comprises the same medium as the reference bioreactor. The method comprises:

receiving, by a comparison unit of a bioreactor state monitoring system a PACO-reference profile, the PACO-reference profile being a representation of the variation in a reference PACO value versus time the PACO-reference profile being indicative of a deviation of a CO2 off gas rate measured in the reference bioreactor from a predicted CO2 off gas rate of the reference bioreactor, the predicted CO2 off gas rate being the predicted off gas rate of said medium in the reference bioreactor in pH-CO2 equilibrium state under absence of the cell culture and under the condition that the pH value of the medium in equilibrium state is identical to the pH value of the reference bioreactor measured when measuring the CO2 off gas rate in the reference bioreactor, the PACO reference profile depending on the amount of CO2 off gas produced by the cells of the cell culture in the reference bioreactor while cultivating the cell culture;

receiving, by the comparison unit, a data object comprising a medium-specific relation, the medium-specific relation being specific for the medium and indicating a relation between the pH value of the medium and a respective fraction of CO2 gas in a gas volume when said medium is in pH-CO2 equilibrium state with said gas volume and lacks the cell culture;

repeatedly receiving, at a current time, a current CO2 off gas rate of the bioreactor and a current pH value of the medium of the bioreactor measured during the cultivation of the cell culture in the bioreactor;

computing, by the comparison unit, for each of the received current CO2 off gas rates:

a PACO value, the PACO-value being indicative of a deviation of a CO2 off gas rate measured in the bioreactor from a predicted CO2 off gas rate, the predicted CO2 off gas rate being the predicted off gas rate of said medium in pH-CO2 equilibrium state in the bioreactor under absence of the cell culture and under the condition that the pH value of the medium in equilibrium state is identical to the pH value of the bioreactor (104, 106) measured when measuring the CO2 off gas rate in the bioreactor, the PACO value depending on the amount of CO2 off gas produced by the cells of the cell culture in the bioreactor while cultivating the cell culture, the computation of the PACO value using as input.

the received current CO2 off gas rate;

the received current pH value;

the total gas inflow rate of the bioreactor at the time of receiving the current CO2 off gas rate; and the medium-specific relation;

a difference between the computed PACO value and a respective reference PACO value in the PACO-reference profile;

Outputting, by the comparison unit, the computed difference, the computed difference being indicative of a deviation of the state of the cell culture in the bioreactor from the reference state.

According to embodiments, the PACO reference profile comprising a plurality of reference PACO values. The method further comprises calculating the reference PACO values by:

receiving a data object comprising the medium-specific relation;

repeatedly receiving, at a current time, a current CO2 off gas rate of the reference bioreactor in $$\left[\frac{mol}{min}\right]$$

and a current pH value of the medium of the reference bioreactor measured at said current time during the cultivation of the cell culture in the reference bioreactor;

computing, for each of the received pairs of a current CO2-off gas rate and a current pH value, one of the reference PACO values, the computation of the reference PACO value using as input:

the received current CO2 off gas rate of the reference bioreactor;

the received current pH value of the reference bioreactor;

the total gas inflow rate of the reference bioreactor at the time of receiving the current CO2 off gas rate; and the medium-specific relation.

For example, the reference PACO values can be calculated by the comparison unit that compares the reference PACO profile with the currently calculated PACO values of the monitored and/or controlled bioreactor. Alternatively, the reference PACO values of the reference PACO profile can be calculated by a different data processing unit, e.g. a control computer of the reference bioreactor.

According to embodiments, the method further comprises creating the PACO-reference profile of the reference bioreactor by:

plotting the reference PACO values in an CO2 off gas rate versus time plot;

fitting a curve in the plotted reference PACO values, said curve constituting the reference PACO profile.

Depending on the embodiment, the plotting and fitting may be performed fully automatically by a computer or other data processing device, semi-automatically or manually. The obtained reference PACO profile may be stored on a non-transitory storage medium, e.g. in the form of an electronic data structure. The monitoring unit of the monitored and/or controlled bioreactor may automatically receive said data structure via a network or by reading said data structure from the storage.

According to embodiments, the computation of each of the reference PACO values $PACO_{R\text{-}ti}$ at respective current times ti in time comprising computing, for each of the received current CO2 off gas rates $ACO_{R\text{-}M\text{-}ti}$ and pH values of the reference bioreactor:

an expected CO2 off gas fraction $FCO2_{R\text{-}EXP\text{-}ti}[\%]$ of a current outgas volume of the reference bioreactor according to: $FCO2_{R\text{-}EXP\text{-}ti}[\%]=REL\text{-}M1$, wherein $FCO2_{R\text{-}EXP\text{-}ti}[\%]$ is a predicted CO2 off gas fraction of the total off gas volume of the reference bioreactor in % at the current time, the prediction being calculated, by using the received current pH value as input for REL-M1 ($pH_{R\text{-}ti}$), wherein REL-M1 is the medium-specific relation of the medium (M1), wherein $pH_{R\text{-}ti}$ is the received current pH value in the medium of the reference bioreactor at a time ti, thus, the expected CO2 off gas fraction in the reference bioreactor is computed under the assumption that the medium of the reference bioreactor lacks the cell culture, has the pH value used as input of the medium-specific relation and is in pH-CO2 equilibrium state with the gas phase in the bioreactor above said medium and thus is also in equilibrium with the total off gas volume of said bioreactor;

an expected CO2 off gas rate $ACO_{R\text{-}EXP\text{-}ti}$ [mol/min] value according to:

$$ACO_{R-EXP-ti}[\text{mol/min}] = \left(\frac{FCO2_{R-EXP-ti}[\%]}{100}\right) \times TGI_R\left[\frac{\text{mol}}{\text{min}}\right],$$

wherein the $ACO_{R\text{-}EXP\text{-}ti}$ [mol/min] value is the expected CO2 off gas rate of the reference bioreactor (102) in $$\left[\frac{\text{mol}}{\text{min}}\right],$$

wherein the $TGI_R$ is the total amount of gas influx of the reference bioreactor (102) at the current time ti, the $$PACO_{R-ti}\left[\frac{\text{mol}}{\text{min}}\right]$$

value according to: $PACO_{R\text{-}ti}=ACO_{R\text{-}EXP\text{-}ti}$ [mol/min]–$ACO_{R\text{-}M\text{-}ti}$ [mol/min], wherein $ACO_{R\text{-}M\text{-}ti}$ [mol/min] is the CO2 off gas rate in $$\left[\frac{\text{mol}}{\text{min}}\right]$$

measured at time ti in the reference bioreactor.

In general terms, the PACO value of a particular bioreactor (e.g. the reference bioreactor or monitored bioreactor B1 or B2) at a particular time $t_i$ is computed as: $PACO_{ti}=ACO_{EXP\text{-}ti}–ACO_{MEASURED\text{-}ti}$, wherein $ACO_{EXP\text{-}ti}$ is the "predicted" (or "expected") CO2 off gas rate of said medium at time $t_i$ in said bioreactor in pH-CO2 equilibrium state under absence of the cell culture and under the condition that the pH value of the medium in equilibrium state is identical to the current pH value of the bioreactor measured when measuring the CO2 off gas rate in the bioreactor. For example, the predicted CO2 off gas rate can be obtained by inputting the received current pH value of the bioreactor at time ti into the medium-specific relation. The measured CO2 off gas rate can be obtained from a CO2 measuring device. The predicted CO2 off gas rate and the measured CO2 off gas rate can have the unit [mol CO2/min].

The expected/predicted CO2 off gas rate of the reference bioreactor thus represents a kind of "cell-free CO2 off gas rate" predicted for the medium at a pH value provided as input, the medium lacking the cell culture cells and any other components which could modify the pH-CO2 equilibrium state of the medium.

A "pH measuring device" as used herein is a device and/or substance used for measuring a current pH value in a medium. A pH measuring device can be, for example, a pH indicator (like phenolphthalein)—in form of a solution or pH strips—or a potentiometric apparatus. According to preferred embodiments, the pH measuring device is a pH-meter. The pH-meter can be, for example, a continuous pH-meter, i.e., a pH-meter capable of continuously and repeatedly measuring the pH of the medium of a bioreactor without having to draw samples and without having to insert said pH-meter in the medium for each individual measurement. For example, a pH measuring device can be a precise voltmeter, connected to the medium and to a reference electrode, and scaled in such a way that it displays not the measured potential, but ready pH value. Preferentially, the pH measuring device is immersed in the medium and is used for repeatedly measuring the current pH value in the medium during the whole time while cultivating cells in the bioreactor. For example, the pH measuring device may measure a current pH value every minute, or every 30 minutes, or every hour. In typical today's pH-meters used as pH measuring devices, a reference electrode is built into the pH electrode, which makes the device compact.

An "Online-measurement" as used herein is a process of obtaining a measurement value being descriptive of state features of a bioreactor or of a cell culture contained therein, whereby the duration required for performing the measurement is shorter than the time during which said features significantly change. A significant change can be a change by more than a predefined threshold value. For example, a change by more than 5% may be considered as a significant change. The threshold may vary for different features. Online-measurements may allow controlling a bioreactor in real time.

An "Offline-measurement" is a process of obtaining a measurement value being descriptive of state features of a bioreactor or of a cell culture contained therein, whereby the duration required for performing the measurement is longer than the time during which said features significantly change. A significant change can be a change by more than a predefined threshold value. For example, a change by more than 5% may be considered as a significant change. A typical example for an offline-measurement is the automated, semi-automated or manual sampling of a probe of the medium e.g. for measuring a current pH value. Offline measurements are based on a discontinuous sampling process. As the bioreactor features may meanwhile have changed since the sample was taken, controlling the bioreactor based on offline-measurement data tends to be of low quality due to significant latency times between the moment of measurement and the moment of performing a respective control operation.

According to embodiments, the current pH value of the monitored and/or controlled bioreactor is measured by a continuous pH measuring device, e.g. a pH-meter immersed in the medium of said bioreactor. In addition or alternatively, the current pH value of the reference bioreactor is measured by a continuous pH measuring device, e.g. a pH-meter immersed in the medium of said reference bioreactor.

A "CO2 measuring device", also referred to as "CO2 meter" or "CO2 analyzer" is a device used for measuring a current CO2 concentration in a gas volume, e.g. the gas volume above the medium of a bioreactor or the off gas of a bioreactor. According to embodiments, the current CO2 off gas rate of the monitored and/or controlled bioreactor is measured by a continuous CO2 off gas meter, i.e., a device capable of measuring the current CO2 concentration in the off gas of a bioreactor repeatedly without having to insert or replace a hardware module into the bioreactor or its connected off gas pipe or pipes for each CO2 concentration measurement. In combination with the total gas influx rate or total off gas rate, the CO2 off gas rate can be determined automatically by the CO2 off gas meter or a data processing device connected to said CO2 off gas meter. In addition or alternatively, the current CO2 off gas rate of the reference bioreactor is measured by a continuous CO2 off gas meter. The measured current off gas rate can be mathematically derived from a current CO2 concentration in the off gas of the bioreactor and a current total off gas volume of the bioreactor. Nevertheless, a such derived CO2 off gas rate is referred herein as a "measured CO2 off gas rate" as it can be easily computed from the measured CO2 concentration and the total gas influx rate (or total off gas rate). According to some embodiments, said computation in addition uses the volume or mass of the respective bioreactor as input for normalizing the calculated CO2 off gas rate in a way that the impact of the volume of the medium is leveled out.

Using continuous pH measuring devices and/or continuous CO2 off gas meters may be advantageous as each PACO value or reference PACO value can be derived from parameters which can be measured easily and repeatedly. Many existing bioreactors already comprise one or more immersed pH-meters and/or comprise or are coupled with measurement devices capable of measuring the CO2 off gas rate and/or the total gas influx rate. Depending on the embodiment, the bioreactor (or reference bioreactor) comprises a single gas inflow line or pipe or multiple gas inflow lines or pipes. For example, a single gas inflow line or pipe may be used for delivering environmental air or (already expanded) compressed air from special suppliers into the bioreactor (reference bioreactor). Said environmental air or compressed air may consist of a mixture of gasses, in particular N2, O2 and CO2 that is typical for the earth's atmosphere. In addition or alternatively, the single gas inflow line or pipe or any of the other gas inflow lines or pipes may be used for delivering individual gases such as N2, O2 and CO2 to the bioreactor, e.g. to control the cell growth. In any case, the total gas influx rate is determined, e.g. the total amount of all gasses delivered to a bioreactor per time unit via any of the gas inflow lines or pipes of a bioreactor.

According to embodiments, the bioreactor (the monitored and/or controlled bioreactor and/or the reference bioreactor) comprises one or more microspargers for generating very finely dispersed gas bubbles from the inflowing gas for accelerating the establishment of a pH-CO2 equilibrium between the medium and the gas volume in the bioreactor. For example, a microsparger may be used for an influx gas mix or for each individual influx gas component separately. In addition, or alternatively, one or each of the two bioreactors is configured and operated such that the carbon dioxide and one or more other gases (e.g. nitrogen, oxygen and/or air) are added together simultaneously to the bioreactor as a gas mix. For example, all influx gases may be input to the bioreactor as gas mix, e.g. via a submersed pipe opening or a microsparger.

Preferentially, all process gases are input to the bioreactor via a microsparger and/or in the form of a gas mix in case the volume of the bioreactor is below a threshold volume of e.g. 400 liter or e.g. 200 liter.

According to embodiments, the aeration rate and bubble size of the influx gases in the medium of the bioreactor is chosen such that all gas bubbles reach pH-CO2 equilibrium with the medium before leaving the bioreactor or are dissolved completely in the medium.

Said features may be advantageous as they ensure that the gas bubbles reach equilibrium state before their gas content leaves the bioreactor a microsparger generates very finely dispersed gas bubbles of the inflowing gas, thereby accelerating the establishment of a pH-CO2 equilibrium between the medium and the gas volume in the bioreactor. Inputting the CO2 gas as a gas mix avoids the situation that the CO2 transition rate from a pure CO2 gas bubble into the medium is larger than the CO2 transition rate from the medium to e.g. air or N2 bubbles (the transition rate may depend on the amount of CO2 concentration difference between medium and different types of bubbles). Thus, said measures ensure the comparability of the state of bioreactors over a wide range of bioreactor volumes, including volumes below e.g. 400 liter.

According to embodiments, the reference PACO profile comprises at least one reference PACO value having been obtained for the reference bioreactor (by measuring a current pH value and a current CO2 off gas rate) at a time $t_{R-0}$ in time when the medium in the reference bioreactor has reached pH-CO2 equilibrium at a particular temperature and pressure before the reference bioreactor is inoculated with the cell culture. The predefined temperature and pressure in the reference bioreactor at time $t_{R-0}$ must be identical to the temperature and pressure of the medium sample(s) used for empirically determining the medium-specific relation, e.g. 20° C. and normal atmospheric pressure. Said reference PACO value is referred to as "initialization reference PACO value".

When the monitored and/or controlled bioreactor is initiated, a current PACO value is obtained from said bioreactor (by measuring a current pH value and a current CO2 off gas rate) at a time $t_{B1-0}$ when the medium in said bioreactor has reached pH-CO2 equilibrium at the same temperature and pressure like the reference bioreactor at $t_{R-0}$. Said current PACO value is referred to as "initialization PACO value" of the monitored and/or controlled bioreactor.

The initialization of the monitored and/or controlled bioreactor comprises comparing the initialization reference PACO value with the initialization PACO value of the monitored and/or controlled bioreactor. In case the comparison returns that the difference between said two compared PACO values exceeds a predefined threshold, e.g. 5% of the smaller one of the two compared initialization PACO values, it is determined that the pH-measuring device of the monitored bioreactor is calibrated erroneously or is defect. Also, in case the two bioreactors are in pH-CO2 equilibrium state at the same temperature and pressure and have been set to the same pH value (e.g. by choosing the CO2 influx rate accordingly), but have a different CO2 concentration in the off gas, it is determined that the pH measuring devices of the two bioreactors have been calibrated differently. Thereby, it is assumed that the two bioreactors comprise the same cell-free medium and that the CO2 analyzers are calibrated correctly. For example, the comparison and the determination may be executed manually. More preferentially, said comparison and determination is executed automatically by a data processing system, e.g. a computer. The computer may generate and output a warning message being indicative of a calibration error of the monitored and/or controlled bioreactor and/or may automatically initiate a calibration of the pH-measuring device of the monitored and/or controlled bioreactor.

This may have the advantageous effect that the initialization of a bioreactor comprising a wrongly calibrated pH measuring device can be prohibited from the beginning. A wrongly calibrated pH measuring device can result in poor performance of the cell culture and even in a complete failure of the biological or biochemical processes which should take place in the bioreactor, because the wrong pH values will result in erroneous PACO values and may result in errors control signals which depend on the calculated difference of the currently obtained PACO values with reference PACO values. Media and cell culture cells are expensive, so preventing the inoculation of a bioreactor in case of pH measuring device calibration errors may save time and costs associated with operating a cell culture in a bioreactor under erroneous control parameters and/or may allow take appropriate corrective actions, e.g. exchanging the wrongly calibrated or defect pH measuring device.

In a further aspect, the invention relates to method for testing the calibration of a pH-meter. The method comprises:
  receiving, at a time ti before a medium of a bioreactor is inoculated with a cell culture, a current, measured pH-value of the medium from a pH measuring device and receiving a current, measured CO2 off gas rate of the bioreactor, the bioreactor having a predefined pressure and temperature;
  receiving a medium-specific relation, the medium-specific relation being specific for the type of medium and indicating a relation between the pH value of the medium and a respective fraction of CO2 gas in a gas volume when said medium is in pH-CO2 equilibrium state with said gas volume and lacks a cell culture;
  using the current, measured pH-value as input to the relation for predicting the current CO2 off gas rate of the bioreactor expected for the medium in the bioreactor in pH-CO2 equilibrium state under absence of the cell culture at the measured current pH value;
  determining a current PACO value, the current PACO value indicating the difference between the current, measured CO2 off gas rate of the bioreactor and the predicted CO2 off gas rate of the bioreactor;
  determining a difference between a reference PACO value and the determined, current PACO value of the bioreactor, the reference PACO value being indicative of a deviation of a CO2 off gas rate measured in the reference bioreactor from a predicted CO2 off gas rate of the reference bioreactor, the predicted CO2 off gas rate being the predicted off gas rate of said type of medium in the reference bioreactor in pH-CO2 equilibrium state under absence of the cell culture and under the condition that the pH value of the medium in equilibrium state is identical to the pH value of the reference bioreactor measured when measuring the CO2 off gas rate in the reference bioreactor;
  if the determined difference exceeds a threshold value, determining that the pH-measuring device is erroneously calibrated.

Alternatively, instead of comparing PACO values, the CO2 concentration of the off gas of the two bioreactors and the pH values of the medium in the two bioreactors are compared to determine if the pH measuring devices of the two compared bioreactors were calibrated identically. The two bioreactors are initiated and filled with the same cell-free medium at the same pressure and temperature and a current pH value and a current CO2 concentration of the medium in the two bioreactors are measured and compared when the two bioreactors have reached pH-CO2 equilibrium. If the CO2 concentration in the off gas of the two bioreactors is identical while the pH value is not, or if the pH values of the two bioreactors is identical and the CO2 concentration in the off gas is not, the comparison unit automatically determines that the two bioreactors were calibrated differently and initiates appropriate actions, e.g. outputs a warning message or initiates the replacement or a recalibration of a pH measuring device.

This may have the advantage that it is possible to determine calibration errors of the pH measuring device before a bioreactor is inoculated with a cell culture, thereby preventing the waste of time and effort involved with cultivating cells in a bioreactor over multiple days with sub-optimal, pH dependent control parameters.

According to embodiments, the pH calibration test method is used for testing if a pH measuring device of the monitored and/or controlled bioreactor is calibrated correctly before inoculating the bioreactor with the cell culture. The method comprises determining that the difference does not exceed the threshold value, determining that the pH-measuring device of the bioreactor is correctly calibrated, and selectively inoculating the bioreactor with the cell culture in case the pH-measuring device is determined to be calibrated correctly. After inoculation of the cell culture in the monitored and/or controlled bioreactor, said bioreactor is monitored and/or controlled by minimizing a difference of a dynamically calculated PACO value of said bioreactor and a reference PACO value specified in a reference PACO profile.

The predefined temperature and pressure in the bioreactor at the time ti are identical to the temperature and pressure of one or more samples of the medium having been previously used for empirically determining the medium-specific relation.

According to some embodiments, the following value pairs of the reference bioreactor 102 and a monitored and/or controlled bioreactor are compared at a time after inoculation of the cell culture:
  the respectively computed PACO values or the respectively measured CO2 concentrations in the off gas of the two bioreactors;
  the pH values of the medium in the two bioreactors;
  the oxygen uptake rate (OUR) of the cell culture in the respective bioreactors.

The OUR is considered as an indicator of the state of the metabolism of a cell culture. The two bioreactors are operated at the same pressure and temperature. The CO2 off gas concentration and/or the PACO value may be influenced by the metabolism of the cell cultures. The current CO2 off gas concentrations or PACO values and the current pH values and OUR rates are measured and compared when the two bioreactors have reached pH-CO2 equilibrium. If the CO2 concentrations in the off gas of the two bioreactors (or the PACO values) are identical, the two OUR rates are identical while the pH value is not, or if the pH values of the two bioreactors are identical, the OUR rates are identical and the CO2 concentration in the off gas (or PACO values) are not, the comparison unit automatically determines that the two bioreactors were calibrated differently and initiates appropriate actions, e.g. outputs a warning message or initiates the replacement or a recalibration of a pH measuring device.

Said features may be advantageous as they allow to determine any calibration difference between pH measuring devices of two compared bioreactors even in case both bioreactors have been initiated and in case the metabolism of the cells may modify the current pH value. In case the OUR is identical in both bioreactors, any deviation of the PACO or CO2 off gas concentration is considered as a result of a calibration difference not as a result of the cell metabolism.

A "profile" as used herein is a representation of the variation in a parameter value versus time.

A "reference profile" as used herein is a profile having been obtained from a reference bioreactor. The reference profile may have been obtained prior to operating the bioreactor whose cell culture state is to be compared with the cell culture state of the reference bioreactor. For example, the cell culture in the reference bioreactor may be cultivated several month or even years prior to the cultivating of a cell culture in the monitored bioreactor. Alternatively, the cell culture in the reference bioreactor and the cell culture in the "monitored" bioreactor may be cultivated concurrently, thus allowing a "real-time" comparison of the state of the cell cultures in the two compared bioreactors. In some embodiments, the cell culture in the reference bioreactor and the cell culture in the "monitored" bioreactor may be cultivated concurrently but with a time shift, wherein the monitored bioreactor is inoculated with the cell culture later than the reference bioreactor. The delay may be, for example, several hours or even days. Preferentially, when comparing the cell culture state in the monitored and/or controlled bioreactor with the cell culture state in the reference bioreactor, a current PACO value of the monitored bioreactor is compared with a reference PACO value in the reference PACO profile. Thereby, the current PACO value is compared with the one of the reference PACO values in the profile that was obtained after the same time interval—starting from the time of inoculating the cell culture in the respective bioreactor—as the current PACO value of the monitored bioreactor.

The "pH-CO2 equilibrium" indicates a state of a system comprising an aqueous solution (e.g. a cell culture medium) and an air volume above said solution (e.g. the gas volume in a bioreactor) whose pH value and CO2 partial pressure are in chemical equilibrium according to the Henderson-Hasselbalch equation. The CO2 partial pressure corresponds to the fraction of CO2 gas in the total gas volume above the medium. The Henderson-Hasselbalch equation describes the relationship of pH as a measure of acidity with the acid dissociation constant (pKa), in biological and chemical systems. If a gas comprising $CO_2$ is in contact with an aqueous liquid, e.g. a culture medium, at least a small fraction of the CO2 dissolves in said liquid. At room temperature, for example, the solubility of carbon dioxide is about 90 cm³ of $CO_2$ per 100 ml water (c/c, =0.8). Any water-soluble gas becomes more soluble as the temperature decreases. A small fraction (ca. 0.2-1%) of the dissolved $CO_2$ is converted to $H_2CO_3$. Most of the $CO_2$ remains as solvated molecular $CO_2$. This process can be described by the following formulas:

Carbonic Acid (H2CO3) Equilibrium:

[CO2]×[H2O]⇌[H2CO3]⇌[H+]×[HCO3−]

[H+]×[HCO3−]=K×[CO2]×[H2O], wherein
K=equilibrium constant

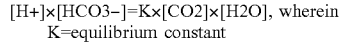
pH=pK+log([HCO3−]/[CO2])

A "medium" or "cell culture medium" is a liquid or gel designed to support the cultivation and typically the growth of microorganisms or cells, or small plants like the moss *Physcomitrella*. There are different media for growing different types of cells. There exist a plurality of different media on the market, e.g. for cell culture of specific cell types derived from plants or animals, and microbiological culture for growing microorganisms, such as bacteria or yeast. A medium may be, for example, a nutrient medium, e.g. an LB medium (Lysogeny Broth), a minimal medium, a selective medium, a differential medium, or an enriched medium. Some media may require a CO2 environment of e.g. 5-10% CO2 to maintain physiological pH. According to some embodiments, the expression "two media being the same" implies that the two media (e.g. the medium in the reference bioreactor on the one hand and the medium in the monitored and/or controlled bioreactor on the other hand) comprise—given a particular pressure, temperature and CO2 concentration in the gas volume above said medium—the same composition and concentration of organic and inorganic compounds and solvents and have been manufactured using the same manufacturing protocols and conditions within the context of measuring accuracy.

According to some embodiments, said expression implies that the two media can differ in respect to any of said criteria (composition, concentration, manufacturing protocol) only in so far as said difference (at a given temperature, pressure and CO2 concentration in the gas volume above said medium) has no or approximately no impact on the pH-CO2 equilibrium of said medium at a plurality of different pH values and in so far as the medium-specific relations derived empirically from said two media respectively are identical.

An "off gas rate", "off-gas rate" or "outgassing rate" as used herein is the amount of gas leaving some entity, e.g. a bioreactor, in unit time. Accordingly, a "CO2 off gas rate" is the amount of CO2 gas leaving said entity in unit time. It may be specified e.g. as [molCO2/min].

A "total gas inflow rate" as used herein is the total amount of gas entering some entity, e.g. a bioreactor, in unit time. The gas may be a mixture of gases. For example, the gas may be environmental air consisting of about 78 Vol. % N2 gas, 21 Vol. % O2 gas and about 1 Vol. % other gases, including about 0.04 Vol. % CO2 gas. It may be specified e.g. as [Liter/min].

A "CO2 volume fraction" as used herein is the fraction of CO2 gas in a total gas volume. The unit may be, for example, Vol. %. It is also referred to as "CO2 concentration" of a gas volume, the concentration being specified in Vol. %.

To "cultivate a cell culture" as used herein typically means that the cells culture is grown, i.e., the number of the cells of the cell culture increases. In some occasions, however, the number of cells may also stagnate or even decline.

BRIEF DESCRIPTION OF THE DRAWINGS

In the following embodiments of the invention are explained in greater detail, by way of example only, making reference to the drawings in which.

DETAILED DESCRIPTION

Figure 1:
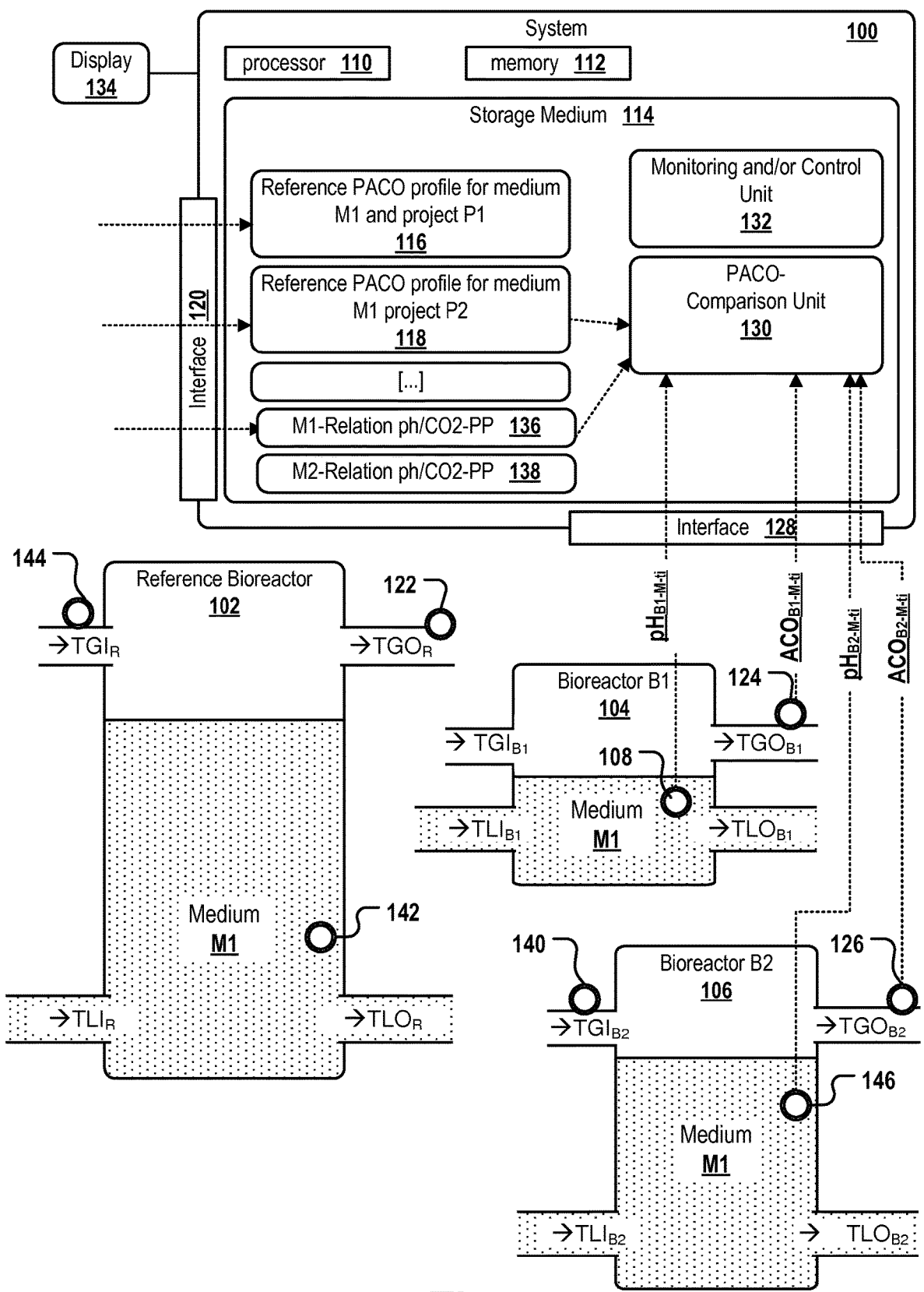
FIG. 1 shows a block diagram of a system for monitoring and/or controlling one or more bioreactors.
Figure 2A:
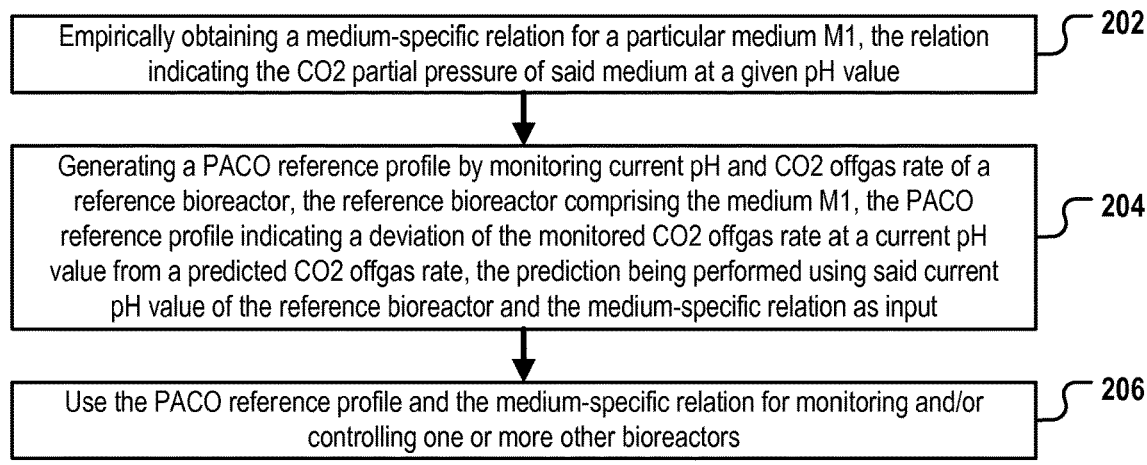
FIG. 2 shows flowcharts of methods for monitoring and/or controlling a bioreactor.

FIG. 1 shows a block diagram of a system 100 for monitoring and/or controlling one or more bioreactors according to an embodiment of the invention. In the following, said embodiment will be described by making reference to a corresponding method for monitoring and/or controlling a bioreactor as indicated in the flow charts of FIGS. 2a and 2b.

FIG. 1 shows a system 100 allowing for real-time and accurate comparison of said culture states of different bioreactors even in case the size, shape, temperature or other engineering or environment parameters of the two compared bioreactors differ from each other. The comparison is based on a so called "PACO" parameter calculated for a particular bioreactor as a derivative of a current pH value and a current CO2 off gas rate of said bioreactor and of a relation 136, 138 being specific for the cell culture medium used in said bioreactor.

The system 100 comprises a processor 110, a main memory 112 and a non-transitory storage medium 114. The storage medium comprises computer readable instructions which, when executed by the processor 110 cause the processor to perform a method for automatically monitoring and/or controlling one or more bioreactors 104, 106 as described for embodiments of the invention.

The storage medium 114 comprises at least one reference PACO profile being specific for a particular medium M1 and a particular project for cultivating a particular cell culture in said medium M1 over a predefined time interval and with a predefined goal. For example, the project could be to grow CHO cells (Chinese hamster ovary cells) over 14 days in the cell culture medium M1 under optimal or nearly optimal cell growth conditions until a cell density of about $100 \times 10^5$ cells/milliliter is reached. In addition, the storage medium 114 comprises a data structure 136, e.g. a file or a database record, being indicative of a pH-CO2-concentration relation that is particular for said cell culture medium M1.

In addition, the storage medium may comprise medium-specific relations 138 of other cell culture media and/or may comprise reference PACO profiles 118 of other cell culture projects with different cell types and/or with a different medium M2. The reference PACO profiles and the medium-specific relations may be received via a data communication interface 120, e.g. a network interface, an USB-port, a CDROM drive or the like. According to some embodiments, the reference PACO profile may be received dynamically for enabling a real-time comparison of the cell culture states of two monitored bioreactors.

The system 100 may further comprise an interface 126 for dynamically receiving current measurement values from one or more monitored and/or controlled bioreactors 104, 106. The measurement values are in particular a current pH value and a current CO2 off gas rate. A PACO comparison unit 130 uses the received measurement values and the medium-specific relation 136 of the medium M1 in the monitored bioreactor 104, 106 for repeatedly calculating current PACO values and comparing said current PACO values to a PACO reference profile 116 of a cell culture project in a reference bioreactor 102 that shall be repeated in the monitored bioreactor 104. Any difference in the current PACO values from respective reference PACO values can be displayed to a user via a display device 134, e.g. a computer monitor or a monitor of a smartphone.

Optionally, the system 100 further comprises a control unit 132 that controls one or more parameters of the bioreactors 104, 106 such that the difference of the currently obtained PACO values from a respective reference PACO value is minimized. The control unit can be, for example, a software and/or hardware module being operatively coupled to the comparison unit 130 for receiving the results of the PACO value comparison. The control unit is capable of controlling the configuration and operation of one or more engineering processes and parameters. For example, the control unit 132 may be operable to increase or decrease the influx of liquids having an impact on the pH value, e.g. may increase or decrease the influx of a citric acid or of a 1M NaOH solution.

The medium M1 can be, for example, Kaighn's Modification of Ham's F-12 Medium comprising, for example, putrescine, thymidine, hypoxanthine, zinc, and higher levels of all amino acids and sodium pyruvate. These additions allow the medium to be supplemented with very low levels of serum or defined components, for some cell types. Ham's F-12K (Kaighn's) Medium contains no proteins or growth factors, and is therefore often supplemented with growth factors and Fetal Bovine Serum (FBS) that may be optimized for a particular cell line. Ham's F-12K (Kaighn's) Medium uses a sodium bicarbonate buffer system (2.5 g/L).

The medium M2 may be an LB medium, and there may exist reference profiles for a plurality of other media M3, M4, e.g. for cultivating bacteria or plants for a variety of purposes and corresponding "projects".

The system is operatively coupled to one or more bioreactors 104 106 which are to be monitored and/or controlled. The dimensions and other engineering parameters (stirring rate and configuration, bubble size, dimension, etc.) of the monitored or controlled bioreactors may differ from each other and/or may differ from the respective parameters of the reference bioreactor. The operative coupling may comprise the sending of monitoring data (current pH and CO2 off gas rates) to the comparison unit 130 and optionally also the sending of control data from the control unit 132 to the respective bioreactor 104, 106. The reference bioreactor may but does not have to be coupled to the system 100. It is sufficient that the PACO reference profile gathered from the reference bioreactor is accessible by the comparison unit 130.

In the following paragraphs, an overview is given how the system 100 and a corresponding method according to embodiments of an invention allows to control the operation of a bioreactor 104, 106 comprising a medium M1 in a way that the cell culture in said bioreactor is cultivated under almost identical physiological conditions as a reference cell culture cultivated in a reference bioreactor in the same medium even in case the dimension and other engineering parameters of said two bioreactors differ.

In a first step 202, a medium specific relation 136 between a pH value of a cell-free medium and a corresponding CO2 partial pressure in an air volume above said medium when the medium is in ph-CO2 equilibrium state at predefined conditions (e.g. 20° C. and normal atmospheric pressure) is empirically determined. This step is described in greater detail in FIGS. 5D) and 6. As the goal is to grow CHO cells for 14 days in Kaighn's Modification of Ham's F-12 Medium, a relation is determined specifically for said medium.

In step 204, a reference PACO profile is obtained from the reference bioreactor 102. At first, the reference bioreactor is filled with the cell-free medium M1 and is initiated by starting continuously adding gas, e.g. by transporting environmental air and/or its individual components (N2, O2 and/or CO2) to the bioreactor and optionally also by starting continuously adding liquids (the cell-free medium, optionally additional liquids such as feed, bases, etc.). In addition, the stirrers may be started. The reference bioreactor may be operated at a temperature and pressure that differs from the temperature and pressure used for obtaining the medium-specific relation. After some time (typically minutes or hours), the medium in the reference bioreactor and the air volume in the reference bioreactor above the medium will have reached pH-CO2 equilibrium state and one or more PACO values are calculated for the reference bioreactor from the medium-specific relation 136 and current pH- and CO2 values of the reference bioreactor.

According to embodiments, during the generation of the reference PACO profile, the reference bioreactor is fed with one or more liquids such as a feeding solution or a base in addition to a cell-free medium. In this case, additional reference profiles are generated in some embodiments. Said additional profiles respectively indicate the amount of feeding solution or base added to the reference bioreactor at a given moment in time of the profile. When initiating and operating the monitored and/or controlled bioreactor, the same amount of feeding solution or base per volume unit of the medium and per unit time is added to said bioreactor as specified in the respective profiles. Thus, it is ensured that even in case the composition of the medium in the bioreactor changes, the medium in the bioreactor is "the same" or "approximately the same" as in the reference bioreactor at a given moment in time ti. As the feeding solution and/or the base typically does not significantly modify the composition of the medium, the medium-specific relation can be used for computing the current PACO values even in case the medium specific relation was empirically determined for a medium lacking said feeding solution. If, however, the composition of the medium in the reference bioreactor should dramatically change while cultivating the cells in the reference medium, e.g. because of a switch from a first medium to another, second medium of a completely different composition, in fact two consecutive PACO reference plots and two different media-specific relations need to be determined and transferred to a control unit of the monitored and/or controlled bioreactor.

Preferentially, the monitored and/or controlled bioreactor 104, 106 at least at the time point of initialization is operated under the same temperature and pressure as the reference bioreactor. However, it is possible that while operating the bioreactor 104, 106, the temperature and/or pressure is modified in order to minimize PACO difference.

Then in step 206, the PACO reference profile and the medium-specific relation 136 are used for monitoring and/or controlling the cell culture state in a different bioreactor 104, 106, e.g. by transferring the obtained reference PACO profile and the relation 136 via the Internet or via a portable storage medium to the system 100 and storing the profile and the relation in the storage medium 114. As can be inferred from FIG. 1, the one or more monitored bioreactors 104, 106 may differ from the reference bioreactor 102 in respect to many parameters, e.g. the size and shape of the bioreactor, stirring parameters, total gas influx rate, the temperature, the pressure, the surface speed, bubble size and distribution, and other parameters.

Figure 2B:
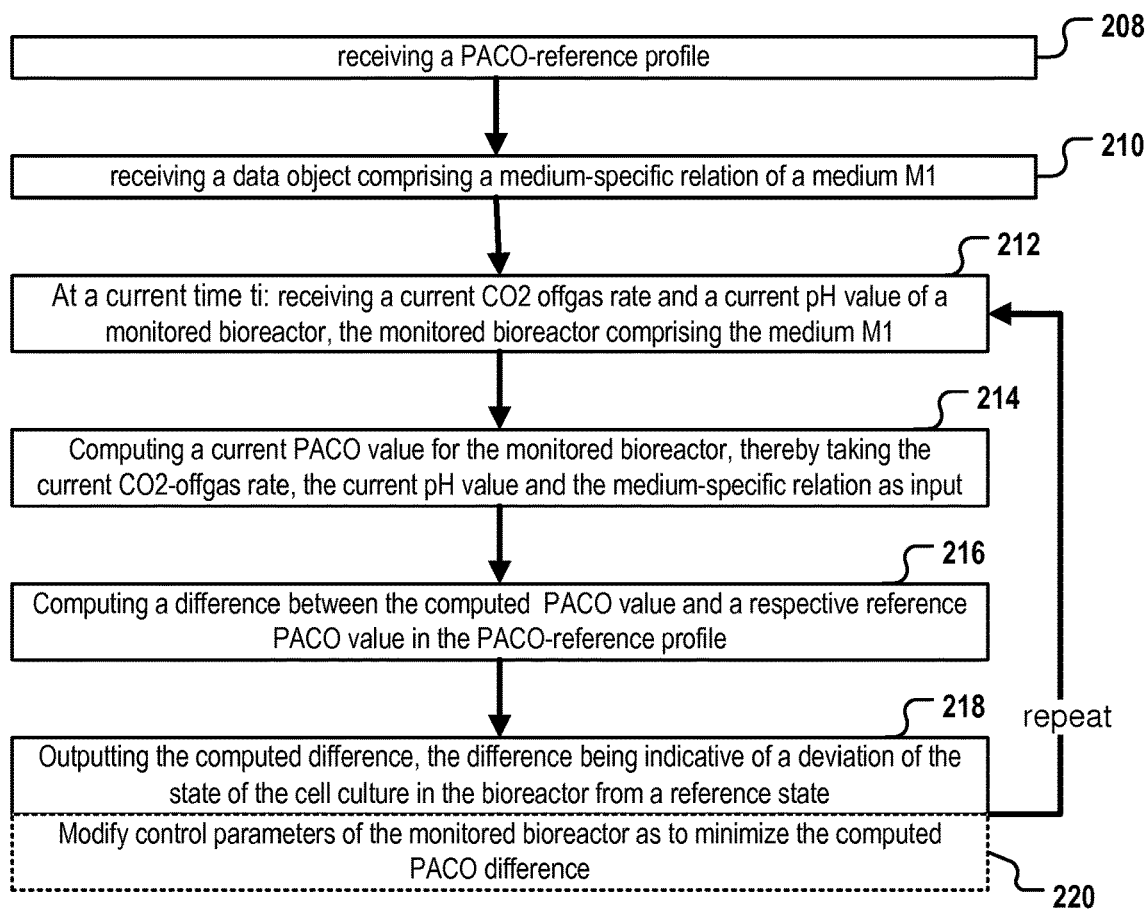

The use 206 of the PACO reference profile in embodiments of the invention may comprise the steps 208-220 depicted in FIG. 2b.

The system 100 is capable of monitoring a state of a cell culture in a bioreactor 104, 106 and comparing the cell culture state of said bioreactor with the cell culture state in the reference bioreactor at a corresponding time after inoculation. The reference bioreactor and each of the monitored bioreactors 104, 106 comprise the same medium M1 and are inoculated with the same type of cell culture. The reference PACO profile may be gathered from the reference bioreactor before the monitored bioreactor(s) are initialized and inoculated with a cell culture, but it is also possible that the reference bioreactor and the one or more monitored bioreactors are operated in parallel or with a delay of e.g. one or more days. In this case, the reference PACO profile is received dynamically while cultivating the cell culture in the monitored bioreactor.

In a first step 208, the comparison unit 130 of the bioreactor state monitoring system 100 receives the PACO-reference profile 116, e.g. by reading a file comprising the profile from the storage medium 114 or receiving said profile via the interface 120 from a system-external data source, e.g. the Internet. The PACO-reference profile is a representation of the variation in a PACO-reference value $PACO_{R\text{-}ti}$ versus time ti, i indicating one of a series of times, e.g. t0, t1, t2, . . . , tmax. The time t0 is preferentially a time point lying a predefined time interval before the time point of inoculating the reference bioreactor with the cell culture. For example, t0 may represent 1 h before inoculation of the reference bioreactor, t1 may represent 45 minutes before inoculation, t2 may represent 30 minutes before inoculation, t3 may represent 15 minutes before inoculation, t4 may represent the time of inoculation, t6 may represent 15 minutes after inoculation and so on until tmax is reached at the end of duration of the cell culture project.

Moreover, the PACO-reference profile is indicative of a deviation of a CO2 off gas rate measured in the reference bioreactor from a predicted CO2 off gas rate for said reference bioreactor. The measured CO2 off gas rate can be obtained by measuring the CO2 concentration of the reference bioreactor and the total gas influx rate $TGI_{R\text{-}ti}$ of the reference bioreactor at a given time. The predicted CO2 off gas rate is the derived by inputting the currently measured pH value $pH_{R\text{-}M\text{-}ti}$ of the medium in the reference bioreactor into the medium-specific relation, thereby assuming said medium would be cell-free and is in pH-CO2 equilibrium state under the predefined temperature and pressure (e.g. 20° C. and normal atmospheric pressure) used when generating the medium-specific relation. Thus, the PACO reference profile is indicative of a deviation of the expected from the measured CO2 off gas rate and depends on the amount of CO2 off gas produced by the cells of the cell culture in the reference bioreactor while cultivating the cell culture and depends on other factors having an impact on the pH-CO2 equilibrium such as temperature, pH, pressure, and the like.

In step 210, the comparison unit 130 receives a data object comprising a medium-specific relation 136 of the medium M1 in the bioreactor 104, 106 to be monitored. The medium-specific relation indicates a relation between multiple different pH values of the medium M1 lacking the cell culture and respective CO2 fraction in a gas volume in pH-CO2 equilibrium state with said medium at the predefined pressure and temperature.

In step 212, the comparison unit 130 repeatedly receives, at a current time ti, a current CO2 off gas rate $ACO_{B1-M-ti}$ of the monitored bioreactor 104 and a current pH value $pH_{B1-ti}$ of the medium M1 of the bioreactor 104 via the interface 128. The measured CO2 off gas rates and pH values are received at least during the cultivation of the cell culture in the bioreactor 104, and may optionally be received already before inoculation to compare the state of the bioreactors in a cell free state.

For each of the received pairs of CO2 off gas rates and pH values in the bioreactor 104, the comparison unit 130 in step 214 computes a PACO value $PACO_{B1-ti}$. The PACO-value is indicative of a deviation of a CO2 off gas rate measured in the bioreactor 104 from a predicted CO2 off gas rate. Said predicted CO2 off gas rate is derived from the CO2 fraction predicted for the gas volume above a sample of said medium M1 in pH-CO2 equilibrium state with said volume under absence of the cell culture, under the predefined temperature and pressure and under the condition that the pH value of the medium in equilibrium state is identical to the pH value of the monitored bioreactor 104 at the time ti. The computed PACO value is indicative of the deviation of the predicted CO2 off gas rate produced by the cells of the cell culture in the bioreactor at a particular time ti while cultivating the cell culture from the CO2 off gas rate actually measured at that time. The computation of the PACO value uses as input:
the received current CO2 off gas rate of the monitored bioreactor 104 at time ti;
the received current pH value rate of the monitored bioreactor 104 at time ti;
the total gas inflow rate $TGI_{B1}$ of the bioreactor 104 at the time ti; and
the medium-specific relation 136 of the medium M1;

In step 216, the comparison unit 130 computes a difference between the computed PACO value $PACO_{B1-ti}$ of the monitored bioreactor 104 and a respective reference PACO value $PACO_{R-ti}$ in the PACO-reference profile 116. For example, the $PACO_{B1-t100}$ of the monitored bioreactor 104 is compared with a respective $PACO_{R-t100}$ in the PACO-reference profile 116, whereby t100 corresponds to the begin of the $24^{th}$ hour after inoculation.

In step 220, the comparison unit 130 outputs the computed difference, e.g. on the display 134. The computed difference is indicative of a deviation of the state of the cell culture in the bioreactor 104 from the reference state of the cell culture in the reference bioreactor 102 according to profile 116.

According to embodiments, the comparison unit 130 or a control unit coupled to the comparison unit may in addition monitor the state of one or more additional bioreactors 106 as described above.

Figure 3:
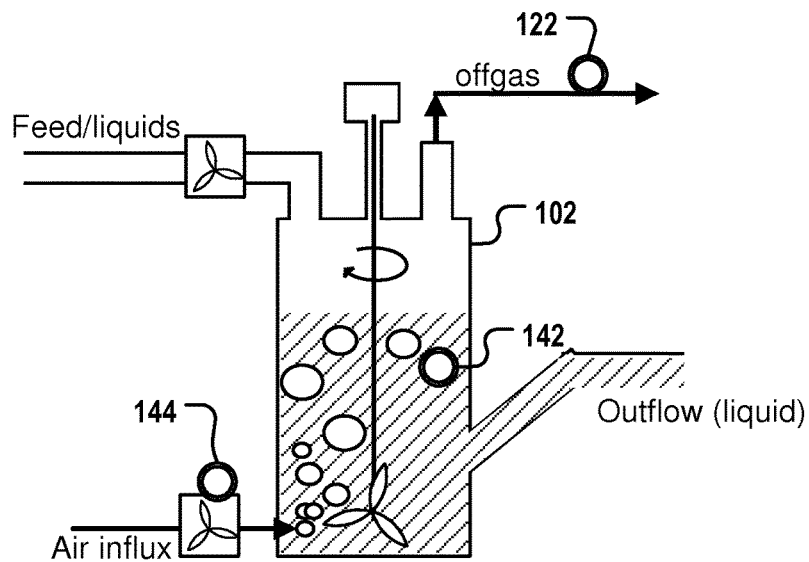
FIG. 3 shows components of a bioreactor.

FIG. 3 shows an embodiment of a bioreactor 102, 104, 106. The bioreactor is coupled to a first pipe for transferring liquids such as acids, bases, fresh medium, and the like into the bioreactor and to an outflow. The bioreactor is in addition coupled to one or more second pipes for transferring gases, e.g. environmental air and/or N2 gas and/or O2 gas and/or CO2 gas into the bioreactor and is coupled to a third pipe for the off gas. The second pipe may comprise a sensor 144 for determining a current total gas influx rate. The third pipe may comprise a sensor 122, e.g. a CO2 off gas analyzer, to selectively measure the amount of CO2 gas transferred through the third pipe per time unit. According to other embodiments, there may be not pipes for the influx and outflux of liquids and nutrients may be fed to the bioreactor by means of step-wise bolus addition of a feed solution.

Figure 4:
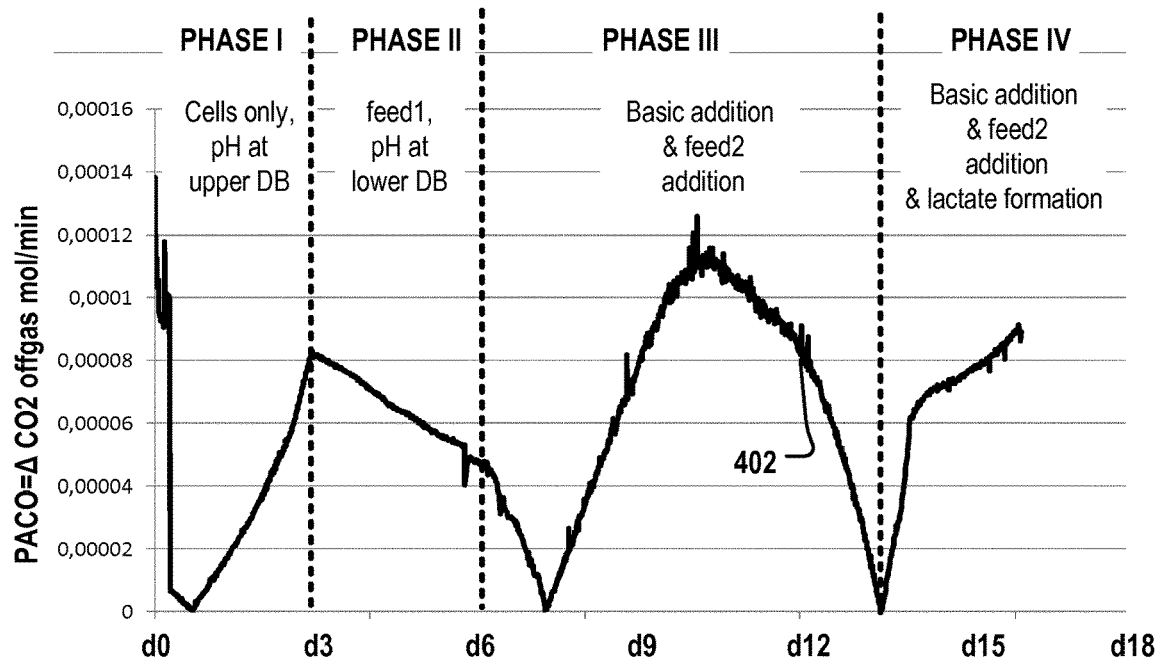
FIG. 4 shows various phases of cultivating and growing a cell culture.

FIG. 4 shows various phases of cultivating and growing a cell culture in a reference bioreactor 102 according to a particular cell culture project (e.g. growing CHO cells over 18 days) and a PACO reference profile 402 having been derived from said project. During the project, different feeds (feed 1, feed 2, feed 3) and/or basic liquids were added and the impact of the PACO value in the reference PACO profile is shown. In order to reproduce the project in another bioreactor 104, 106, the same feeds and/or basic substances have to be added to the culture medium at respective time intervals, and any deviations of the PACO values in the monitored bioreactor 104 from respective reference PACO values in the profile 402 are determined and optionally minimized by modifying engineering parameters and configurations of the monitored and controlled bioreactor 104, 106.

The PACO profile 402 depicted in FIG. 4 clearly shows different process phases that can be observed when growing the set culture in the reference bioreactor 102 during that project. Thus, the profile shows that a single parameter, the PACO parameter computed from easily and dynamically derivable measurement values can identify different process phases correlating with different states of the cell culture cells. Nevertheless, the PACO value does not quantify single effects of individual parameters (basic feed, base addition, lactate production, etc.) having an impact on the pH-CO2 equilibrium of the medium M1 in the reference bioreactor 102.

As can be seen in FIG. 4, the growing of said culture cells after inoculation leads to an increased difference in the measured version of a predicted CO2 off gas rate ("ACO") (CO2 off gas rate), measured e.g. in [mol CO2/min]). While growing the cells, the pH of the medium typically decreases and the CO2 off gas rate may increase in dependence on the decrease of the pH value and other parameters. The profile 402 covers four different phases: in a first phase following inoculation, no feed is added and the PACO value rises. The rise may be caused by the cell metabolism. In a second phase, a first feed is added to the medium and the PACO value decreases. Then, in a third phase, a second, basic feed is added that increases the PACO value. Later in said "third feed" phase, however, the cell metabolism results in a reduction of the PACO value and the cell culture may enter a fourth phase. In the fourth phase, the second, basic feed is still added to the medium M1. In addition, the cell culture cells start to produce lactate and/or other substances which decrease the pH value of the medium. As a result, the PACO value of the reference bioreactor rises in the fourth phase.

The "lower DB" indicates the lowest allowed pH value of the medium. In case the pH value of the medium falls below the "lower DB" threshold, a controller unit may automatically decrease CO2 influx rate in order to increase the pH value. The "upper DB" indicates the highest allowed pH value of the medium. In case the pH value of the medium exceeds the "upper DB" threshold, a controller unit may automatically increase CO2 influx rate in order to increase the pH value. In-between said thresholds, the control of the CO2 influx rate may be controlled solely based on the PACO value.

FIG. 4 shows that when growing a cell culture, the actual CO2 concentration will significantly differ from the CO2 concentration expected for the cell-free medium because base addition, feed addition, lactate generation, different CO2 accumulation and removal rates in the medium and so on will affect the pH-CO2 equilibrium of the medium and the CO2 concentration in a gas volume above said medium in a bioreactor.

Figure 5:
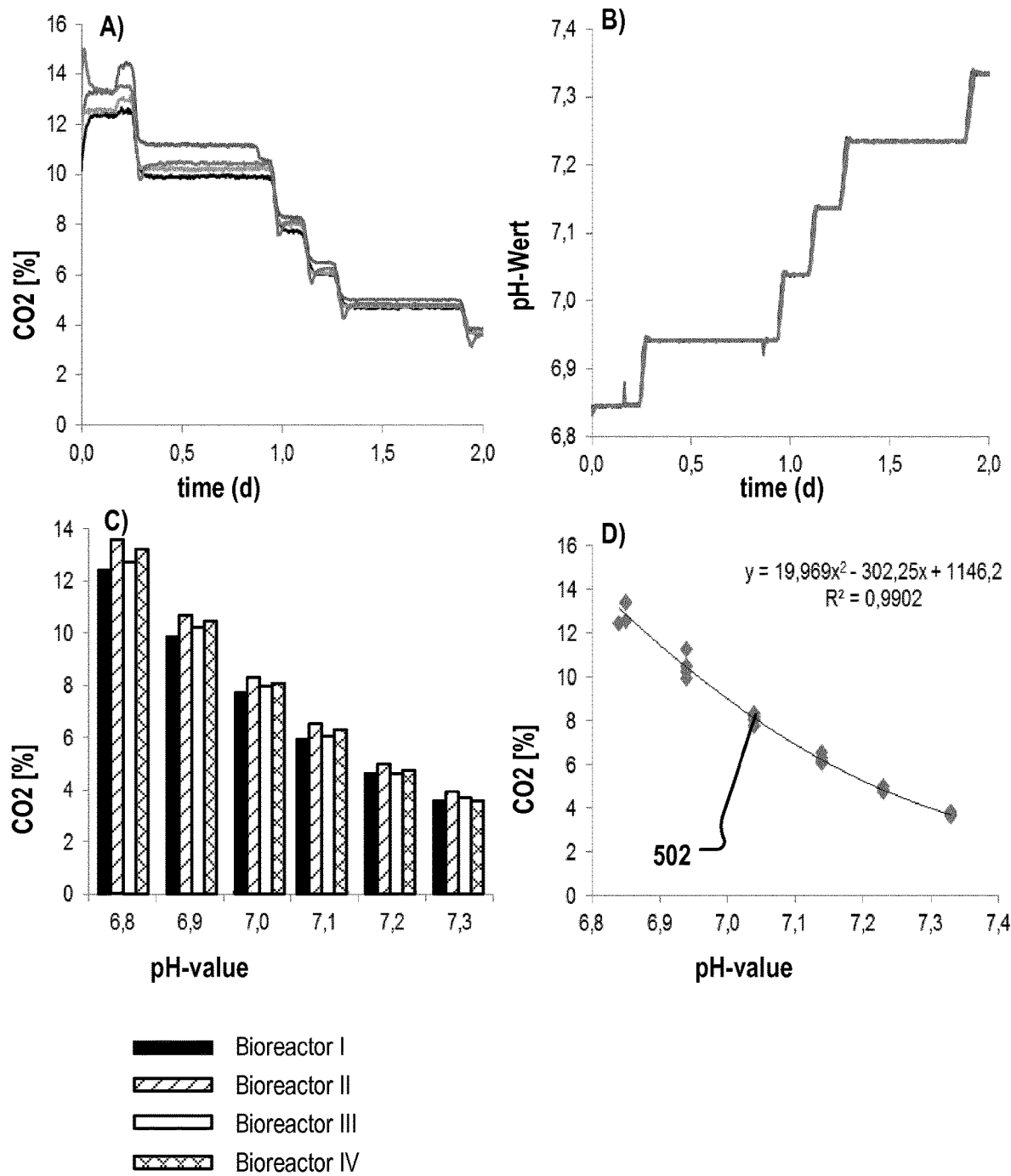
FIG. 5 shows diagrams illustrating the dependence of the CO2 concentration in the off gas of a bioreactor from other parameters.

FIG. 5 shows diagrams A, B, C and D illustrating the dependence of the CO2 concentration in the off gas (and thus, implicitly, the off gas rates) of four different bioreactors from the pH value and the independence of said CO2 concentration of engineering- and size parameters of the respective bioreactors.

The four different bioreactors have the following engineering properties:

|  | Bioreactor I | Bioreactor II | Bioreactor III | Bioreactor IV |
|---|---|---|---|---|
| Total volume (volume of medium + gasphase) | 0.94 L | 1.2 L | 1.5 L | 1.8 L |
| Aeration rate | 26.3 mL/L/min | 20.8 mL/L/min | 16.6 mL/L/min | 13.8 mL/L/min |
| Number of stirrers | 1 | 1 | 2 | 2 |

Each of said bioreactors I-IV was filled with a particular cell culture medium M1 which did not comprise any cells. The original pH value of said medium was 6.85 (see diagram B). Then, the pH value was increased in each of the bioreactors by decreasing the CO2 concentration in the gas volume above said medium in the respective bioreactor. At the beginning of the test and for each of a set of predefined pH values, the medium in each bioreactor was allowed to reach pH-CO2 equilibrium with the gas volume above the medium at a predefined temperature and pressure, e.g. 20° C. and normal atmospheric pressure. After that equilibrium was reached, the CO2 concentration in Vol. % of the total off gas ("fraction CO2 gas"–"FCO2 [%]", "CO2 concentration") was determined for each of said four bioreactors (see diagram A showing, in combination with diagram B, the impact of the pH-value on the measured CO2 concentration in the off gas). Diagram C) shows the impact of the 15 pH-value on the measured CO2 concentration of each of the four bioreactors in the form of a bar chart. The maximum deviation of the FCO2 [%] obtained for each of the four bioreactors was less than 0.4% of the total off gas rate of the bioreactor.

The diagram D) is a plot comprising the CO2 [%] values measured at each of the four bioreactors I-IV at each of the set pH values (6.85, 6.95, 7.05, 7.15, 7.25, 7.35) at a time when the medium M1 of said bioreactor reached pH-CO2 equilibrium state.

It should be noted that the pH-CO2 equilibrium in a bioreactor may be challenged by the rate of CO2 gas entering and/or leaving the bioreactor, so the pH-CO2 equilibrium may in fact be a dynamic equilibrium. Nevertheless, it is possible to control a bioreactor in a manner that the dynamic pH-CO2 equilibrium is established at a particular pH value, e.g. by decreasing or increasing the CO2 concentration in the gas volume above the medium in the bioreactor by modifying the total CO2 influx rate in the bioreactor.

The pH value may be modified by adding acidic or basic substances or liquids. However, as said substances may modify the composition of the medium, preferentially the dynamic pH-CO2 equilibrium state is established in a bioreactor at a particular pH value solely by controlling the CO2 influx rate in a manner that a desired pH value is reached. Using the CO2 influx rate for establishing the pH-CO2 equilibrium rather than a basic or an acidic substance has the advantage that the composition of the medium is not altered (except for the concentration of the solved CO2 and its dissociation products) and thus the medium specific relation can be empirically derived from the same medium at different pH values.

Then, a curve 502 is fitted to the plot in order to empirically determine parameters for a relation 316 being specific for the medium M1 contained in the four bioreactors. This approach allows to empirically determine, for a particular cell culture medium, a medium-specific relation used as input for predicting the CO2 volume fraction expected in a gas phase above said medium when said medium has a particular pH value pressure and temperature (e.g. 20° C. and normal atmospheric pressure), lacks any cells and is in pH-CO2 equilibrium. The obtained relation is independent of bioreactor scale, aeration rate and other engineering parameters in processes that use CO2 gas as acidic component for pH control. The medium-specific relation is determined only once for a particular medium M1. The determination may be performed in a single bioreactor, e.g. in the reference bioreactor before the reference bioreactor is inoculated. In order to increase accuracy, it is also possible to perform the determination in multiple bioreactors or other containers allowing the measurement of a pH value and a CO2 gas fraction (CO2 concentration) and then use the information obtained in the multiple bioreactors or containers for obtaining a more accurate, fitted curve 502. In the example depicted in FIG. 5, four different bioreactors were used for empirically determining a fitted curve 502 and a corresponding, medium-specific relation between equilibrium pH value and equilibrium CO2 concentration.

Figure 6:
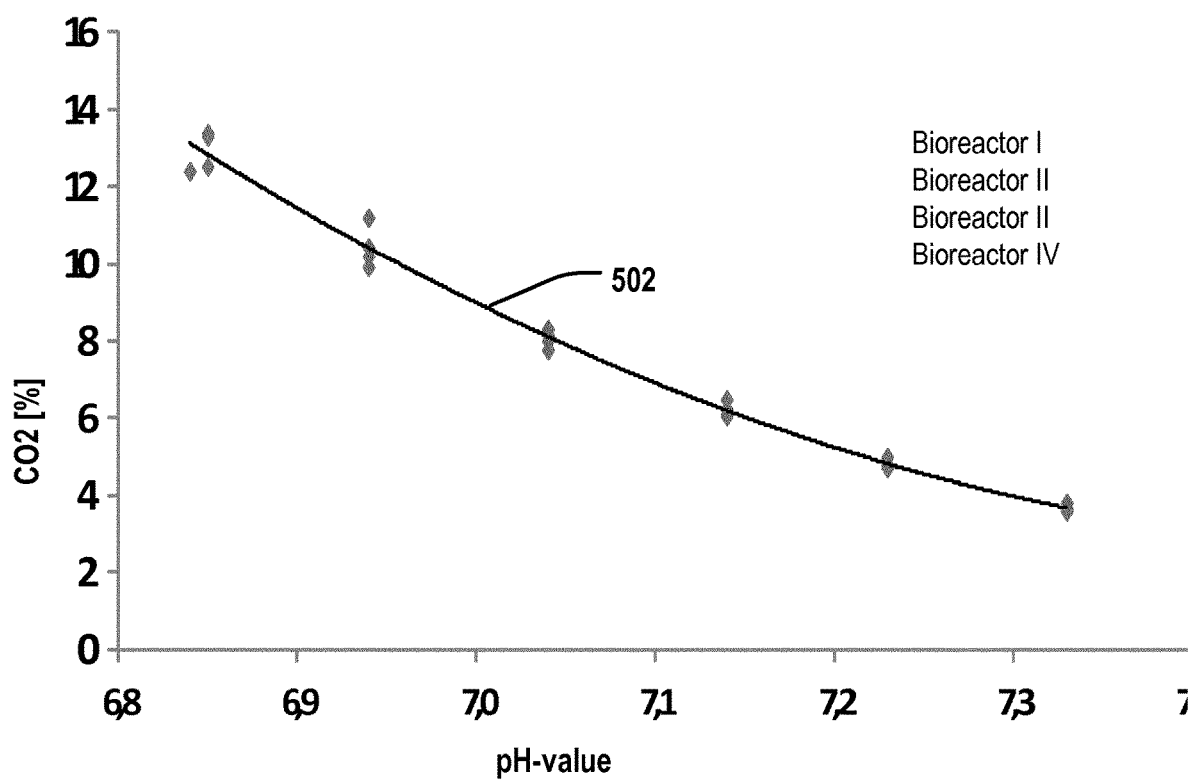
FIG. 6 shows a plot used for obtaining a medium-specific pH-CO2 concentration relation.

FIG. 6 shows the diagram in FIG. 5D) in greater detail. The medium-specific relation 136 of medium M1 is an equation $FCO2_{M1}(pH)=REL-M1(pH)$ obtained by mathematically fitting multiple empirically determined pairs of a pH-value and a respective CO2 concentration in the gas phase above said medium, the CO2 concentration in the gas phase being in pH-CO2 equilibrium with said medium according to the above mentioned Henderson-Hasselbalch equation.

The "FCO2M1(pH)[%]" parameter is the predicted CO2 concentration at the predefined temperature and the predefined pressure in a gas volume in pH-CO2 equilibrium state with said medium having a given pH-value, the prediction being specific for the medium M1 for which the relation was empirically obtained.

The "pH" parameter indicates the pH value used as input of said equation, the input pH value being considered as the pH value of the medium in ph-CO2 equilibrium state of the medium based on which the prediction of the CO2 concentration is performed.

"REL-M1" is a set of one or more parameters a1, a2, b1, b2, b3 connected by operators. The parameters have been obtained by adjusting samples of the medium M1 lacking the cell culture to multiple different pH values as described above, thereby letting the samples reach pH-CO2 equilibrium at the predefined pressure and temperature, by determining the equilibrium CO2 concentrations in respective gas volumes being in contact with the medium in the samples, by plotting the measured equilibrium CO2 concentrations against the respective equilibrium pH values of the samples (see FIGS. 5D and 6), fitting a curve 502 in the plotted values and deriving the parameters a1, a2 or b1, b2, b3 from the fitted curve.

According to some embodiments, the equation $FCO2_{M1}(pH)=REL-M1(pH)$ is a linear equation according to $FCO2_{M1}(pH)[\%]=a1 \times pH+a2$. In this case, the parameters a1 and a2 are the parameters derived from the fitted curve. In the depicted example, a linear fit would yield the following equation:

$FCO2_{M1}(pH)=-19,177 \times pH+143,61$. In this example, $a1=-19,177$ and $a2=143,61$.

According to other embodiments, the equation $FCO2_{M1}(pH)=REL-M1(pH)$ is a polynomial equation according to $FCO2_{M}(pH)[\%]=b1 \times pH^2+b2 \times pH+b3$. In this case, the parameters b1, b2 and b3 are the parameters derived from the fitted curve. In the depicted example, a polynomial fit would yield the following equation:

$FCO2_{M1}(pH)=19.969 \times pH^2-302.25 \times pH+1146.2$.

In this example, $b1=19.969$ and $b2=-302.25$ and $b3=1146.2$. Using a polynomial fit has the advantage that it is more accurate than a linear fit, although a linear fit is already sufficiently accurate for a PACO based cell culture comparison and monitoring.

FIGS. 7a-d illustrate how a PACO value of a bioreactor 104, 106 can be calculated from a medium-specific relation 136 and some easily and dynamically obtainable measurement values.

Figure 7A:
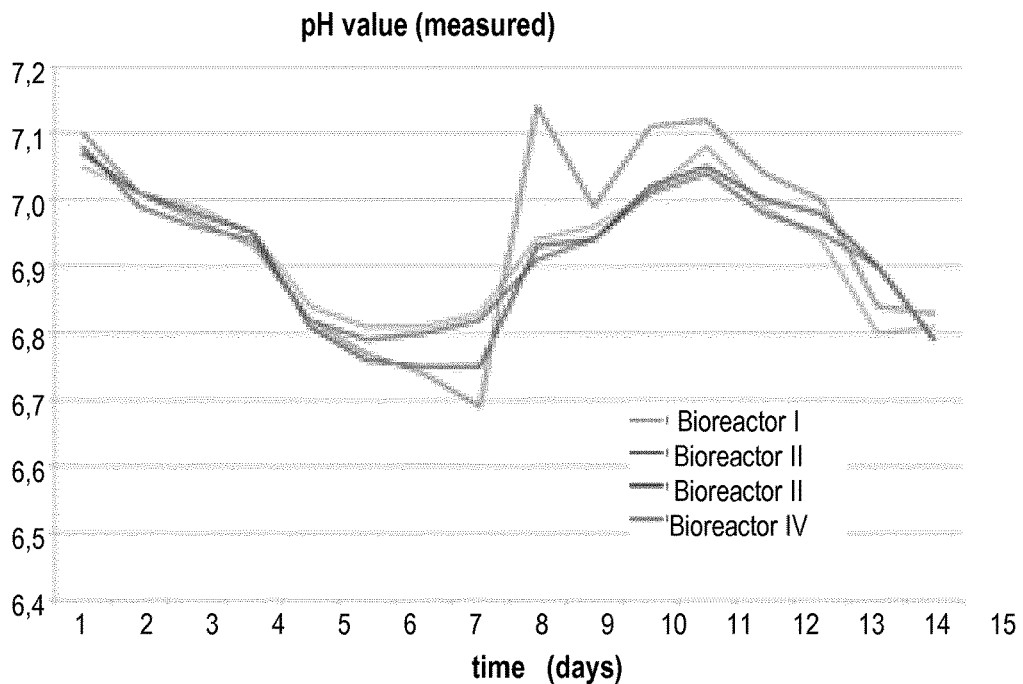
FIG. 7a shows the pH values of four different bioreactors while growing a cell culture in four different bioreactors.

FIG. 7a shows the variation of a pH value measured in four different bioreactors I-IV while growing a cell culture in a particular medium M1 over multiple days. Preferentially, each pH value is measured using a pH-measuring device, e.g. a potentiometric pH-meter, immersed in the medium M1 of the bioreactor at pH-CO2 equilibrium of said medium.

Figure 7B:
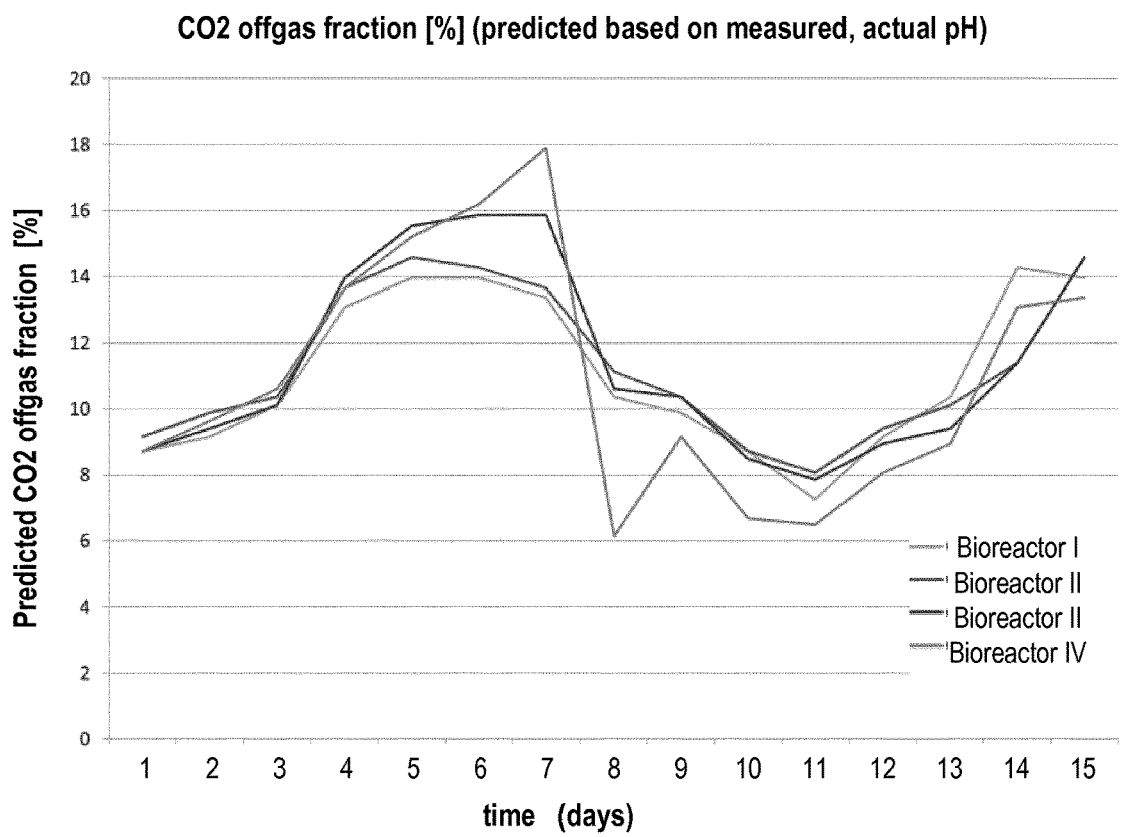
FIG. 7b shows the CO2 fraction in the off gas predicted for each of the four bioreactors using the pH values and the medium-specific relation as input.

FIG. 7b shows the CO2 concentration in [%] of the total off gas of a bioreactor predicted for each of the four bioreactors using the measured, actual pH values of FIG. 7a and the medium-specific relation as input. For example, the medium-specific relation for medium M1 follows a polynomial equation according to $FCO2_{M1}(pH)[\%]=b1 \times pH^2+b2 \times pH+b3$. The parameters b1, b2 and b3 are the parameters derived from the fitted curve depicted in FIGS. 5D and 6.

For example, 4 days after t0 (the start of the project), the pH value measured in all bioreactors is about 6.95. Accordingly, the expected CO2 concentration at the fourth day is calculated by using the pH-value 6.95 as input:

$FCO2_{M1}(pH)[\%]1=b1 \times 6-95^2+b2 \times 6.95+b3$.

B1, b2 and b3 are the empirically determined parameters of the medium M1. The unit [%] means: the fraction of the CO2 outgas volume of the total off gas volume (corresponding to the total gas influx TGI $\left[\frac{mL}{min}\right]$)

of the bioreactor at a particular time.

Figure 7C:
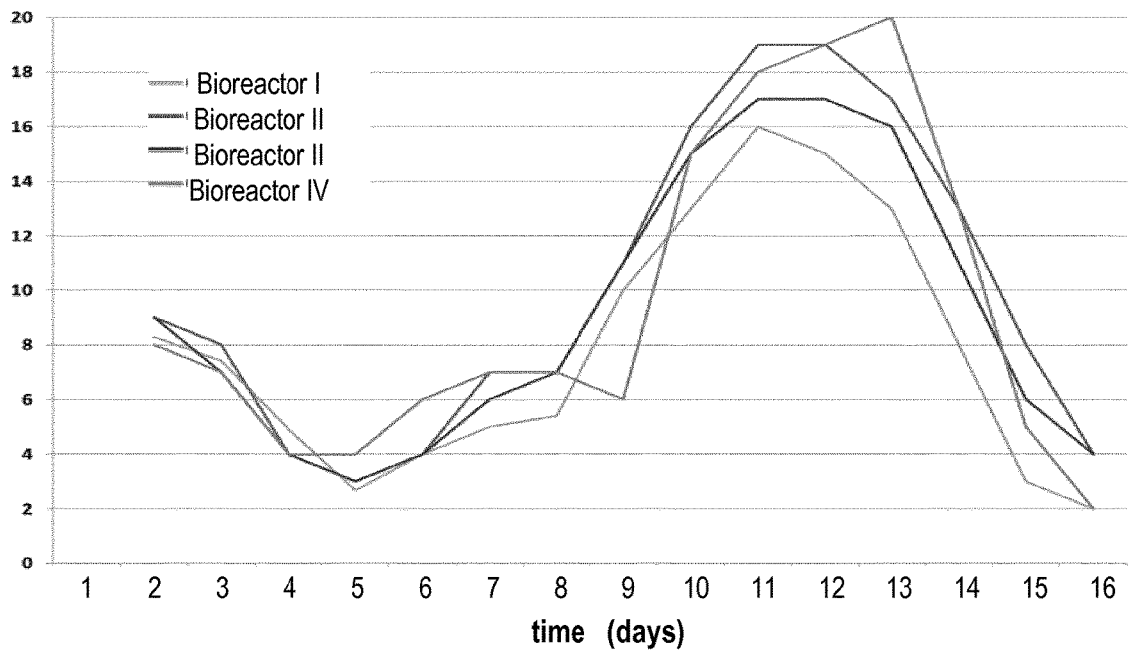
FIG. 7c shows the CO2 off gas fraction actually measured in each of the four bioreactors.

FIG. 7c shows the actual ("measured") CO2 off gas fraction measured in each of the four bioreactors. As can be inferred from a comparison of the predicted CO2 off gas fractions [%] and the actual (measured) CO2 off gas fractions of each bioreactor, significant differences exist which may stem from the impact of the metabolism of the cells in the cell culture and other factors having an impact on the pH-CO2 equilibrium of a medium.

For example, a CO2 analyzer device 122, also referred to as "carbon dioxide sensor" as depicted in FIG. 3 may be used for repeatedly measuring the concentration of CO2 in the off gas per time unit. Common examples for CO2 sensors are infrared gas sensors (NDIR) and chemical gas sensors. NDIR sensors are spectroscopic sensors to detect CO2 in a gaseous environment by its characteristic absorption. Alternatively, the CO2 sensor may be a microelectromechanical sensor.

Figure 7D:
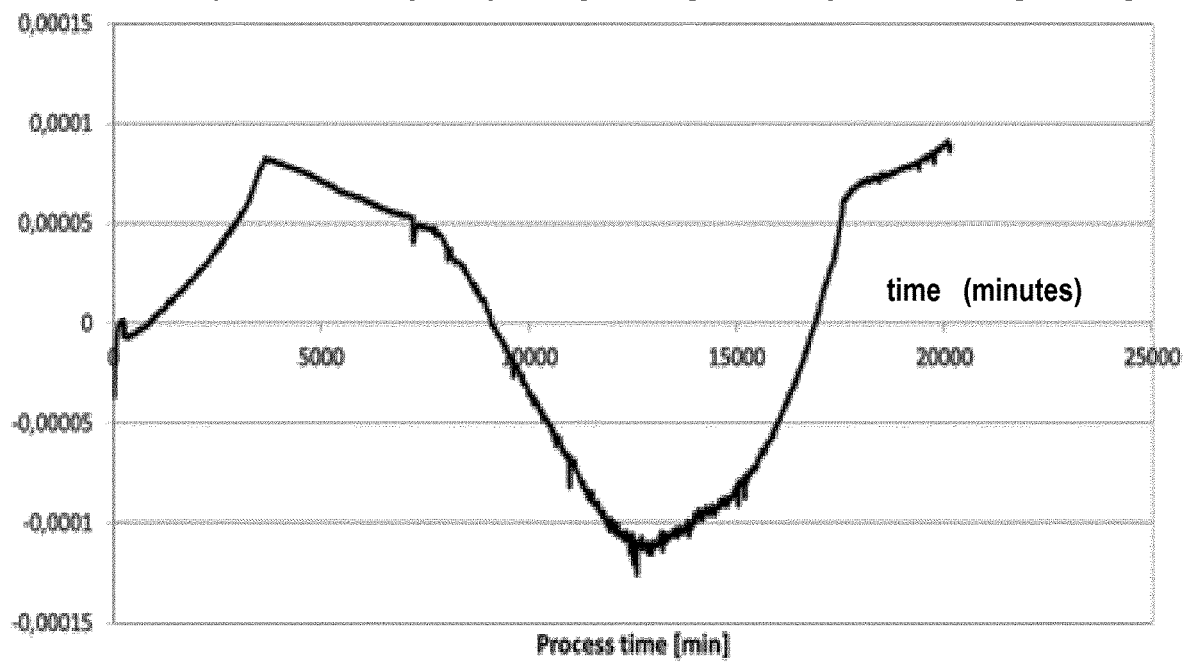
FIG. 7d shows a PACO profile resulting from the difference of the predicted and actually measured CO2 off gas fractions.

FIG. 7d shows a PACO profile of one of the bioreactors generated as the difference of the predicted CO2 off gas concentrations of FIG. 7b and the measured CO2 off gas concentrations of FIG. 7c of said one bioreactor.

To calculate the PACO values of the profile 402, the predicted and measured CO2 off gas concentrations ("CO2" or "FCO2" [%]) are transformed, according to embodiments of the invention, into CO2 off gas rates [mol/min].

For example, the calculation can be performed for each of the measured pH values of FIG. 7a) according to:

Expected CO2 Off Gas Rate:

$$ACO_{M1-EXPECTED}(pH)\left[\frac{mol}{min}\right] = \frac{FCO2_{M1-EXP}(pH)[\%]}{100} = \times \frac{TGI\left[\frac{mL}{min}\right]}{1000 \times 22.414 \left[\frac{L}{mol}\right]}.$$

Measured ("Actual") CO2 Off Gas Rate:

$$ACO_{M1-M}(pH)\left[\frac{mol}{min}\right] = \frac{FCO2_{M1-M}(pH)[\%]}{100} = \times \frac{TGI\left[\frac{mL}{min}\right]}{1000 \times 22.414 \left[\frac{L}{mol}\right]}.$$

Thereby, TGI $\left[\frac{mL}{min}\right]$ is the total off gas volume of the bioreactor for which the current PACO value is calculated, whereby the total amount of gas influx TGI $\left[\frac{mL}{min}\right]$ in the bioreactor may be used as the total off gas volume. In case the total off gas volume of the bioreactor is not constant, the TGI $$\left[\frac{mL}{min}\right]$$

needs to be determined at each time when the pH value used as input for calculating the CO2 off gas rate is measured. For example, in case the bioreactor has a first gas influx pipe for CO2, a second gas influx pipe for O2, a third gas influx pipe for N2 and a fourth gas influx pipe for environmental air, the gas flow in each of the four pipes being individually modifiable, the TGI $$\left[\frac{mL}{min}\right]$$

can be calculated as $$CO2\left[\frac{mL}{min}\right] + O2\left[\frac{mL}{min}\right] + N2\left[\frac{mL}{min}\right] + air\left[\frac{mL}{min}\right].$$

The value 2.414

$$\left[\frac{L}{mol}\right]$$

is the volume of a Mol of an ideal gas.

Then, the PACO value $$\left[\frac{mol}{min}\right]$$

is calculated for each of the measured pH values (corresponding to a time ti) as the difference between the absolute CO2 off gas rate expected at said pH value in a cell-free medium M1 and the actually measured CO2 off gas rate $$\left[\frac{mol}{min}\right]$$

of the bioreactor.

$$PACO_{M1-ti}\left[\frac{mol}{min}\right] = ACO_{M1-EXP}(ti)\left[\frac{mol}{min}\right] - ACO_{M1-M}(ti)\left[\frac{mol}{min}\right].$$

The computation of the PACO value according to the above formulas may have the advantage that the formulas may be validly applied for comparing states of two or more bioreactors having different scales, types or equipment. The PACO value is computed from input data that does not involve an offline measurement. Offset measurements, e.g. for determining the pH value or biomass content of a sample according to previous approaches for determining the state of a bioreactor, might add offsets to the measurement values. Said offsets often depend on the equipment used in the respective plant and production site and thus might be an obstacle in reliably comparing the states of bioreactors located in different production sites. The above formulas thus may provide for an error-robust, global comparison of bioreactor states.

However, the above formula can be adjusted in a lot of ways:
the formula may be modified to include correction factors for the gas volume: the above formula assumes an ideal gas having a mol volume of 22.414 liters at 273.15 K and 1.01325*105 Pa pressure. In reality temperature, pressure and therefore volumes might differ. Therefore correction factors or measured data can be used to adjust formula and accuracy of the output.
the formula may be modified to include correction factors for the measured CO2 off gas concentrations to compensate for pressure effects: thereby, the impact of environmental pressure changes on the CO2 off gas concentration may be compensated for;
the formula may be modified to include correction factors for the humidity of the off gas to compensate for effects of the humidity in the off gas CO2 concentration measurements;
the formula may be modified to include correction factors for the temperature to compensate for effects of the temperature on the pH measurement device used; pH values measured by two or more online pH meters may be received simultaneously and used for computing an average measured pH value for increasing the accuracy of the pH measurement;
the formula may be modified to account for or compensate the effect of probe calibration, the compensation may be implemented e.g. in the form of a compensation curve that, if superimposed on a measured voltage of a pH meter, shifts the measured voltage per unit of modified pH (e.g. mV/pH); the curve may have a slope and amplitude suited for compensating current offsets of a pH measurement obtained from neutral pH probes. As an example, a temperature compensation facility of the pH meter could lead to different pH readings if switched on and off. Alternatively, the pH meter may support different algorithms for computing the pH from a measured voltage difference. All said effects may be compensated by introducing one or more compensation factors in the formula.

Preferentially, the calculation of a reference PACO value is performed in the same way as the calculation of the PACO value, whereby the current pH values and CO2 off gas rates are measured in the reference bioreactor.

According to embodiments, the controller unit controls the monitored bioreactor 104 such that the difference between a PACO value currently calculated for the controlled bioreactor 104 (from a pH value and a CO2 concentration [%] measured at a time ti after inoculation) and a corresponding reference PACO value in a reference profile 402 is minimized.

Normalized PACO Values

According to some embodiments, a normalized PACO value is calculated that takes into account the volume of the medium M1 in the bioreactor for which the PACO value is calculated.

This may allow leveling out different bioreactor volumes and thus may allow to scale a bioreactor process up or down and/or to compare cell cultures of bioreactors having different dimensions.

At first, normalized CO2 off gas rates "$NACO_{M1}$" are calculated according to:

$$NACO_{M1-\text{EXP}}(\text{pH})\left[\frac{\frac{\text{mol}}{\text{min}}}{L}\right] = \frac{\frac{ACO_{M1-\text{EXP}}(\text{pH})[\%]}{100} \times \frac{TGI\left[\frac{\text{mL}}{\text{min}}\right]}{1000 \times 22.414\left[\frac{L}{\text{mol}}\right]}}{\text{volume of medium } M1 \text{ in bioreactor [L]}}$$

$$NACO_{M1-M}(\text{pH})\left[\frac{\frac{\text{mol}}{\text{min}}}{L}\right] = \frac{\frac{ACO_{M1-M}(\text{pH})[\%]}{100} \times \frac{TGI\left[\frac{\text{mL}}{\text{min}}\right]}{1000 \times 22.414\left[\frac{L}{\text{mol}}\right]}}{\text{volume of medium } M1 \text{ in bioreactor [L]}}$$

In case the PACO is calculated for the reference bioreactor 102, the volume of the medium M1 in the bioreactor is the "volume of the medium in the reference bioreactor". In case the PACO is calculated for the monitored and/or controlled bioreactor 104, the volume of the medium M1 in the monitored and/or controlled bioreactor is the "volume of the medium in the bioreactor". Said volume does not comprise the gas phase above the medium.

Then, a volume-normalized PACO value is calculated for a particular time ti when the pH value used for predicting the CO2 off gas value was measured:

$$NPACO_{M1-ti}\left[\frac{\frac{\text{mol}}{\text{min}}}{L}\right] = NACO_{M1-\text{EXP}}(ti)\left[\frac{\frac{\text{mol}}{\text{min}}}{L}\right] - NACO_{M1-M}(ti)\left[\frac{\frac{\text{mol}}{\text{min}}}{L}\right]$$

According to embodiments, the normalized CO2 off gas rates and the PACO values can also be calculated by using the total mass of the medium M1 in the bioreactor instead of the volume of the medium in the bioreactor. Thereby, 1 L of the medium typically corresponds to a mass of 1 kg.

FIG. 7d shows a PACO profile resulting from the difference of the predicted and actually measured CO2 off gas rate.

Figure 8A:
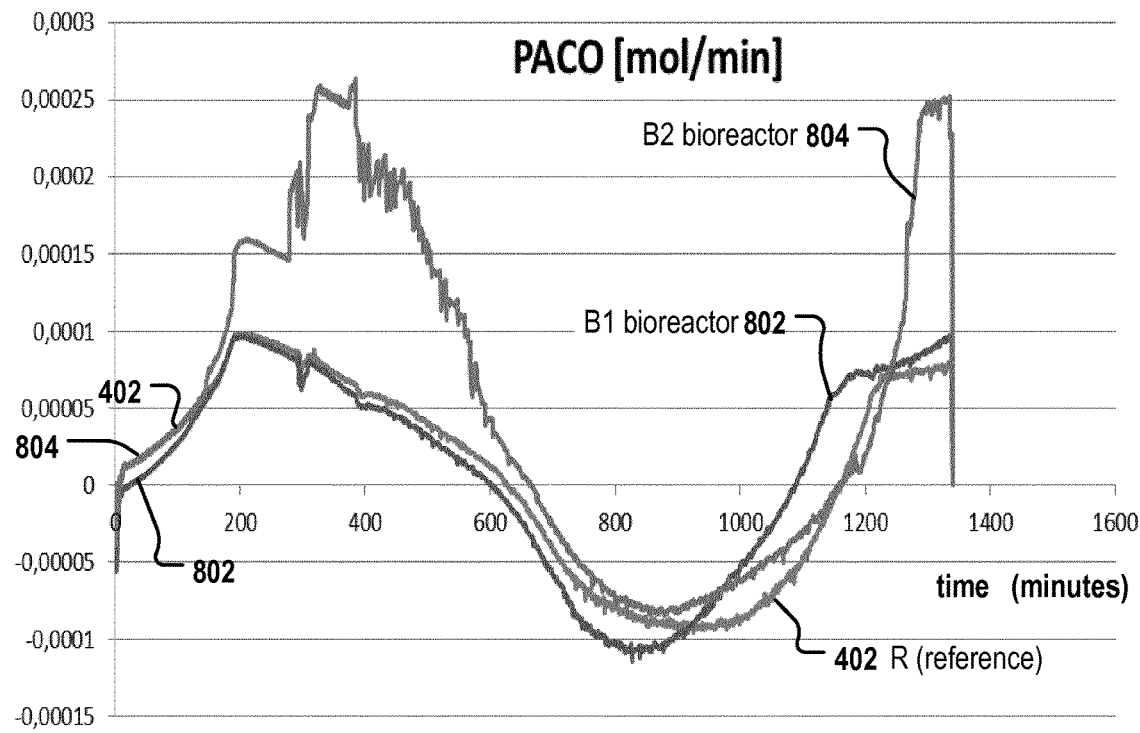
FIG. 8a is a diagram showing PACO profiles of two bioreactors and a reference bioreactor, whereby the PACO profile of one bioreactor differs from the PACO profile of the reference bioreactor already before inoculation.

FIG. 8a is a diagram showing a reference PACO profile 402 of a reference bioreactor 102, a PACO profile 802 of a first monitored and/or controlled bioreactor 104 and a further PACO profile 804 of a second monitored/and controlled bioreactor 106. The diagram indicates that already at time t0 (in the example depicted in FIG. 8 time t0 is the time of inoculation of a bioreactor with the cell culture), the PACO value of the bioreactor 104 ("B1") significantly differs from the PACO value at t0 of the reference bioreactor. According to embodiments, this can be used as an indication that the pH-meters of the bioreactors whose profiles are compared have been calibrated differently. Assuming that the pH measuring device of the reference bioreactor was calibrated correctly, the PACO deviation at t0 (i.e., at or before the medium comprises any cell culture cells which could modulate the PACO), can be used as an indication that the pH measuring device of the monitored bioreactor 106 ("B2"), 104 ("B1") was erroneously calibrated and should be correctly calibrated before starting to grow the cell culture.

In the depicted example, the PACO value of profile 804 of the monitored bioreactor 106 ("B2") at time t0 is identical to the reference PACO value of the reference PACO profile 402 at time t0. The PACO value of profile 802 of the monitored bioreactor 104 ("B4") at time t0 significantly differs the reference PACO value of the reference PACO profile 402 at time t0.

Alternatively, instead of the PACO values, the CO2 concentration of the off gas of the two bioreactors can be compared to determine if the pH measuring devices of the two compared bioreactors were calibrated identically. The two bioreactors are initiated and filled with the same cell-free medium at the same pressure and temperature and a current pH value and a current CO2 concentration of the medium in the two bioreactors are measured and compared when the two bioreactors have reached pH-CO2 equilibrium. If the CO2 concentration in the off gas of the two bioreactors are identical while the pH value are not, or if the pH values of the two bioreactors are identical and the CO2 concentration in the off gas are not, the comparison unit determines that the two bioreactors were calibrated differently.

Wrongly calibrated pH meters may result in inaccurate results when comparing the cell culture states of two cell cultures based on PACO values. This is because the PACO value is a derivative of the pH value. As a consequence, also any action taken by the controller to minimize the PACO difference may fail to minimize the PACO differences (this effect is not shown in FIGS. 8a and 8b, because during the growing of the cell culture in bioreactor B2, the pH-CO2 equilibrium was modified by adding a base and increasing the total gas influx rate; thus, the PACO profile of B2 significantly differs from the reference PACO profile although the pH meters of the reference bioreactor and of bioreactor B2 were calibrated in the same way).

Figure 8B:
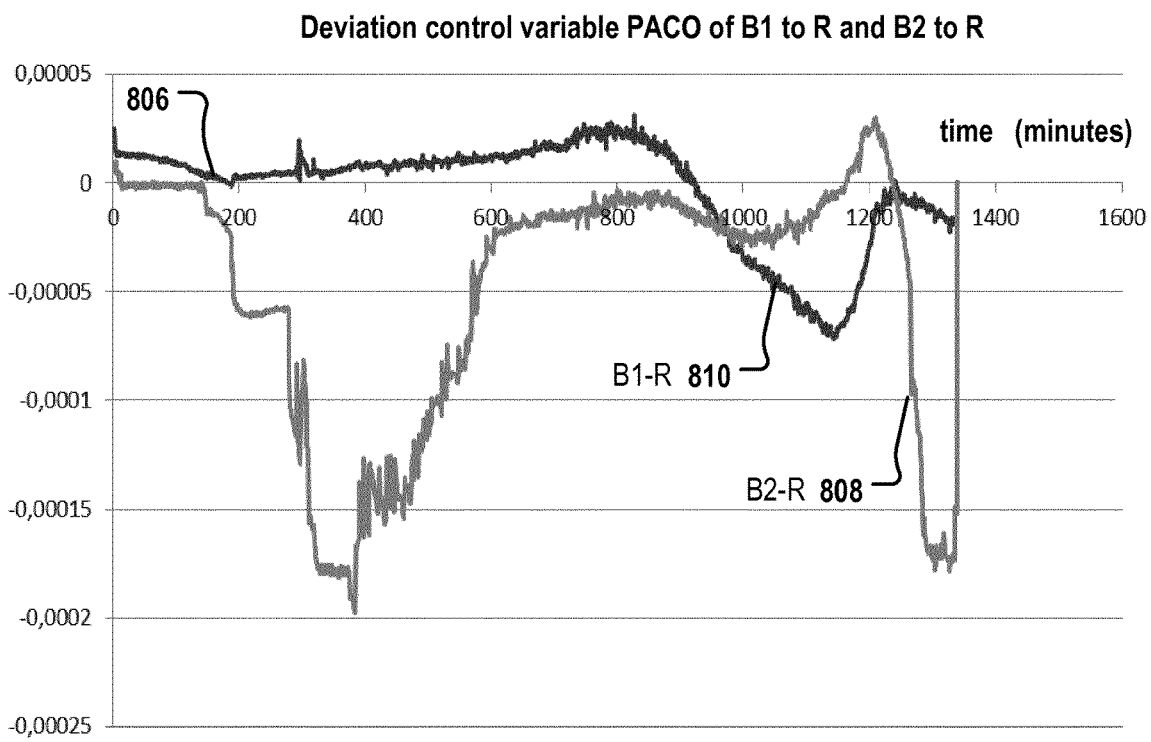
FIG. 8b is a diagram showing the PACO profile differences of the two bioreactors of FIG. 8a to said reference bioreactor.

FIG. 8b is a diagram showing the PACO profile differences of the PACO profiles 802, 804 of two bioreactors 104, 106 to the reference PACO profile 402 of the reference bioreactor 102. Curve 810 represents PACO profile differences of the bioreactor 104 and the reference bioreactor and curve 808 represents PACO profile differences of the bioreactor 106 and the reference bioreactor. The PACO profile differences of the bioreactor 106 to the PACO reference profile 402 are significantly larger than the PACO differences of the bioreactor 104, because while growing the cell culture in B2, the pH-CO2 equilibrium was modified.

LIST OF REFERENCE NUMERALS 100 system for monitoring and/or controlling cell culture states in a bioreactor
102 reference bioreactor
104 monitored and/or controlled bioreactor B1
106 monitored and/or controlled bioreactor B2
108 pH-measuring device
110 processor
112 memory
114 storage medium
116 reference PACO profile
118 reference PACO profile
120 interface for receiving one or more reference PACO profiles and medium-specific relations
122 CO2 off gas analyzer
124 CO2 off gas analyzer
126 CO2 off gas analyzer
128 interface for receiving parameters measured in one or more bioreactors
130 PACO comparison unit
132 control unit
134 display
136 medium-specific relation for medium M1

138 medium-specific relation for medium M2
140 sensor for total gas influx
142 pH-measuring device
144 sensor for total gas influx
146 pH-measuring device
202-220 steps
402 PACO reference profile
502 medium-specific relation plotted for four bioreactors
802 PACO profile of a monitored bioreactor
804 PACO profile of a monitored bioreactor
808 profile difference to reference PACO profile
810 profile difference to reference PACO profile
M1 cell culture medium
$TGI_{B1}$ total gas influx into bioreactor B1
$TGI_{B2}$ total gas influx into bioreactor B2
$TGI_R$ total gas influx into the reference bioreactor
$TGO_{B1}$ total off gas of bioreactor B1
$TGO_{B2}$ total off gas of bioreactor B2
$TGO_R$ total off gas of reference bioreactor
$TLI_{B1}$ total liquid influx into bioreactor B1
$TLI_{B2}$ total liquid influx into bioreactor B2
$TLI_R$ total liquid influx into the reference bioreactor
$TLO_{B1}$ total (liquid) outflow of bioreactor B1
$TLO_{B2}$ total (liquid) outflow of bioreactor B2
$TLO_R$ total (liquid) outflow of reference bioreactor

The invention claimed is:

1. A system for monitoring deviations of a state of a cell culture in a bioreactor from a reference state of a cell culture in a reference bioreactor, the bioreactor comprising a same type of medium as the reference bioreactor, the system comprising:
the bioreactor comprising a medium;
a CO2 off gas analyzer configured to measure a current CO2 off gas rate of the bioreactor;
a pH measurement device configured to measure a current pH value of the medium of the bioreactor;
a non-transitory computer-readable storage medium comprising:
a PACO-reference profile comprising a representation of the variation in a reference PACO value associated with the reference bioreactor versus time, the PACO-reference profile indicating the difference of a CO2 off gas rate measured in the reference bioreactor from a predicted CO2 off gas rate of the reference bioreactor, said predicted CO2 off gas rate in the reference bioreactor being the predicted off gas rate of said medium in the reference bioreactor in pH-CO2 equilibrium state under absence of the cell culture and under the condition that the pH value of the medium in equilibrium state is identical to the pH value of the reference bioreactor measured when measuring the CO2 off gas rate in the reference bioreactor, the PACO reference profile depending on the amount of CO2 off gas produced by the cells of the cell culture in the reference bioreactor while cultivating the cell culture;
a data object comprising a medium-specific relation, the medium-specific relation being specific for the medium and indicating a relation between the pH value of the medium and a respective fraction of CO2 gas in a gas volume when said medium is in pH-CO2 equilibrium state with said gas volume and lacks the cell culture;
an interface for repeatedly receiving, at a current time, the current CO2 off gas rate of the bioreactor and the current pH value of the medium of the bioreactor measured during the cultivation of the cell culture in the bioreactor;
a comparison unit configured to compute, for each of the received current CO2 off gas rates:
a predicted CO2 off gas rate of said medium in said bioreactor in pH-CO2 equilibrium state under absence of the cell culture and under the condition that the pH value of the medium in equilibrium state is identical to the received current pH value of the bioreactor measured when measuring the received current CO2 off gas rate in the bioreactor, the predicted CO2 off gas rate being calculated based on the received current pH value, the medium-specific relation, and a total gas inflow rate of the bioreactor at the time of measuring the received current CO2 off gas rate in the bioreactor,
a computed PACO value comprising a difference of the received current CO2 off gas rate measured in the bioreactor from the predicted CO2 off gas rate at the time of measuring the received current CO2 off gas rate in the bioreactor, the PACO value depending on the amount of CO2 off gas produced by the cells of the cell culture in the bioreactor while cultivating the cell culture,
a difference between the computed PACO value and a respective reference PACO value in the PACO-reference profile, and
outputting the computed difference, the computed difference being indicative of a deviation of the state of the cell culture in the bioreactor from the reference state.

2. The system of claim 1, the medium-specific relation being an equation $FCO2_{M1}(pH)=REL\text{-}M1(pH)$ obtained by mathematically fitting multiple empirically determined pairs of a pH-value of the medium and a respectively measured fraction of CO2 gas in a gas volume, wherein:
$FCO2_{M1}(pH)$ is the predicted fraction of CO2 gas in a gas volume above a sample of the medium when said medium has a given pH-value and is in pH-CO2 equilibrium state with said gas volume and lacks the cell culture;
the pH value is an input parameter value and represents the pH value of the medium in ph-CO2 equilibrium state under the absence of the cell culture;
wherein REL-M1 is a set of one or more parameters connected by operators, the parameters having been obtained by:
adjusting samples of the medium lacking the cell culture, to multiple different pH values, thereby letting the samples reach pH-CO2 equilibrium with the gas volume,
determining the fraction of CO2 gas in a respective gas volume being in ph-CO2 equilibrium with the medium in the samples,
plotting the determined CO2 gas fractions against the respective equilibrium pH values of the samples,
fitting a curve in the plotted values and deriving the parameters of the medium-specific relation from the fitted curve.

3. The system of claim 1, wherein the received current CO2 off gas rate, the received current pH value, the total gas inflow rate of the bioreactor at a particular time and the medium-specific relation are the only input parameters for calculating the computed PACO value for the monitored bioreactor.

4. The system of claim 1, the system being configured to compute the predicted CO2 off gas rate by:
   inputting the received current pH value into the medium-specific-relation to compute a predicted CO2 concentration in the gas volume of the bioreactor in equilibrium state with the medium at the time of measuring the current CO2 off gas rate and the current pH value; and
   multiplying the predicted CO2 concentration with the total gas inflow rate of the bioreactor to obtain the predicted CO2 off gas rate of the bioreactor, the predicted CO2 off gas rate being the predicted off gas rate of said medium in pH-CO2 equilibrium state under absence of the cell culture and under the condition that the pH value of the medium in equilibrium state is identical to the received current pH value input into the medium-specific relation.

5. The system of claim 4, the computation of the predicted CO2 off gas rate of the bioreactor at the current time being performed according to:

$$ACO_{EXP-ti}[\text{mol/min}] = \left(\frac{FCO2_{B1-EXP-ti}\ [\%]}{100}\right) \times TGI_{B1}\left[\frac{\text{mol}}{\text{min}}\right],$$

wherein the $ACO_{EXP-ti}$ is the predicted CO2 off gas rate, wherein the $TGI_{B1}$ is the total amount of gas influx of the bioreactor at the current time, and wherein $FCO2_{EXP}$ is the predicted CO2 concentration in the gas volume of the bioreactor in equilibrium state with the medium at the time of measuring the current CO2 off gas rate and the current pH value.

6. The system of claim 1, the outputting of the computed difference comprising:
   in case the computed difference between the computed PACO value and the respective reference PACO value in the PACO-reference profile exceeds a threshold value, automatically outputting an alarm signal.

7. The system of claim 1, the medium being a carbonate-buffered medium.

8. The system of claim 1, the reference bioreactor differing from the bioreactor in respect to one or more of the following features:
   a) the gas volume in the bioreactor,
   b) the medium volume in the bioreactor,
   c) the Reynolds number of the bioreactor,
   d) the Newton number of the bioreactor,
   e) the dimensions of the bioreactor
   f) geometrical features of the bioreactor and/or bioreactor baffles,
   g) the stirrer configuration
   h) the stirring rate,
   i) the volumetric mass transfer coefficient for oxygen of the bioreactor,
   j) total gas influx rate and/or O2 influx rate and/or N2 influx rate and/or CO2 influx rate,
   k) power input,
   l) pressure in the bioreactor,
   m) gas bubble hold time in the medium,
   n) gas bubble size and distribution in the medium,
   o) surface speed,
   p) a parameter calculated as a derivative from one or more of the parameters a)-o).

9. The system of claim 1, the computation of the predicted CO2 off gas rate at the current time comprising computing, for each of the received current CO2 off gas rates and pH values of the bioreactor:
   an expected CO2 off gas fraction of a current outgas volume of the bioreactor according to: $FCO2_{B1-EXP-ti}[\%]=REL\text{-}M1\ (pH_{B1-ti})$, wherein $FCO2_{B1-EXP-ti}\ [\%]$ is a predicted CO2 off gas fraction of the total off gas volume of the bioreactor in % at the current time, the prediction being calculated by using the received current pH value as input for REL-M1 ($pH_{B1-ti}$), wherein REL-M1 is the medium-specific relation of the medium, wherein $pH_{B1-ti}$ is the received current pH value in the medium of the bioreactor at the current time, and the predicted CO2 off gas rate value according to:

$$ACO_{B1-EXP-ti}[\text{mol/min}] = \left(\frac{FCO2_{B1-EXP-ti}\ [\%]}{100}\right) \times TGI_{B1}\left[\frac{\text{mol}}{\text{min}}\right],$$

wherein the $ACO_{B1-EXP-ti}$ [mol/min] value is the predicted CO2 off gas rate of the bioreactor when the medium of the bioreactor has the currently measured pH value and is in pH-CO2 equilibrium with the gas phase above said medium in $$\left[\frac{\text{mol}}{\text{min}}\right],$$

wherein the $TGI_{B1}$ is the total amount of gas influx of the bioreactor at the current time.

10. The system of claim 1, the medium in the reference bioreactor having a first volume and a first total mass, the medium in the bioreactor having a second volume and a second total mass, the first volume and the second volume differing from each other, the computation of the difference between each one of the computed PACO values and its respective reference PACO value in the PACO-reference profile comprising:
   dividing, by the processor, the computed PACO value by the second volume; and dividing, by the processor, the respective reference PACO value in the PACO-reference profile by the first volume; or
   dividing, by the processor, the computed PACO value by the second mass; and dividing, by the processor, the respective reference PACO value in the PACO-reference profile by the first mass.

11. The system of claim 1, the PACO reference profile covering multiple phases of operating the reference bioreactor, the phases comprising:
   a feed-free phase during which the cell culture is cultivated in the reference bioreactor without feeding;
   a feeding phase during which the cell culture is cultivated in the reference bioreactor in the presence of a given feeding rate, the cell culture not excreting a metabolite affecting the pH value of the medium;
   a feeding phase during which the cell culture is cultivated in the reference bioreactor in the presence of a given feeding rate, the cell culture excreting a metabolite affecting the pH value of the medium.

12. The system of claim 1, the system comprising a control unit configured to automatically modify one or more control parameters of the bioreactor such that the difference between the computed PACO values and the respective reference PACO values in the PACO-reference profile is minimized.

13. The system of claim 12,
wherein in case the computed PACO values are higher than the respective reference PACO values in the PACO reference profile, the control unit is configured to automatically modify one or more control parameters of the bioreactor by performing one or more of the following operations: reduce total air influx rate and/or reduce O2 gas influx rate and/or reduce the CO2 gas influx rate and/or reduce the base influx rate to the bioreactor and/or modify the pressure or the temperature of the bioreactor;

wherein in case the computed PACO values are lower than the respective reference PACO values in the PACO reference profile, the control unit is configured to automatically modify one or more control parameters of the bioreactor by performing one or more of the following operations: increase the total air influx rate and/or increase the O2 gas influx rate and/or increase the CO2 gas influx rate and/or increase the base influx rate to the bioreactor and/or modify the pressure or the temperature of the bioreactor.

14. The system of claim 1, the reference bioreactor differing from the bioreactor in respect to the gas volume in the bioreactor.

15. A method for monitoring deviations of a state of a cell culture in a bioreactor from a reference state of a cell culture in a reference bioreactor, the bioreactor comprising a same type of medium as the reference bioreactor, the method comprising:
repeatedly measuring, by a CO2 off gas analyzer, a current CO2 off gas rate of the bioreactor, the bioreactor comprising a medium;
repeatedly measuring, by a pH measurement device, a current pH value of the medium of the bioreactor;
receiving, by a comparison unit of a bioreactor state monitoring system, a PACO-reference profile, the PACO-reference profile comprising a representation of the variation in a reference PACO value associated with the reference bioreactor versus time, the PACO-reference profile indicating the difference of a CO2 off gas rate measured in the reference bioreactor from a predicted CO2 off gas rate of the reference bioreactor, said predicted CO2 off gas rate being the predicted off gas rate of said medium in the reference bioreactor in pH-CO2 equilibrium state under absence of the cell culture and under the condition that the pH value of the medium in equilibrium state is identical to the pH value of the reference bioreactor measured when measuring the CO2 off gas rate in the reference bioreactor, the PACO reference profile depending on the amount of CO2 off gas produced by the cells of the cell culture in the reference bioreactor while cultivating the cell culture;
receiving, by the comparison unit, a data object comprising a medium-specific relation, the medium-specific relation being specific for the medium and indicating a relation between the pH value of the medium and a respective fraction of CO2 gas in a gas volume when said medium is in pH-CO2 equilibrium state with said gas volume and lacks the cell culture;
repeatedly receiving, at a current time, a current CO2 off gas rate of the bioreactor and a current pH value of the medium of the bioreactor measured during the cultivation of the cell culture in the bioreactor;

computing, by the comparison unit, for each of the received current CO2 off gas rates:
a predicted CO2 off gas rate of said medium in the bioreactor in pH-CO2 equilibrium state under absence of the cell culture and under the condition that the pH value of the medium in equilibrium state is identical to the received current pH value of the bioreactor measured when measuring the received current CO2 off gas rate in the bioreactor, the predicted CO2 off gas rate being calculated based on the received current pH value, the medium-specific relation, and a total gas inflow rate of the bioreactor at the time of measuring the received current CO2 off gas rate in the bioreactor,
a computed PACO value comprising a difference of the received current CO2 off gas rate measured in the bioreactor from the predicted CO2 off gas rate at the time of measuring the received current CO2 off gas rate in the bioreactor, the PACO value depending on the amount of CO2 off gas produced by the cells of the cell culture in the bioreactor while cultivating the cell culture, and
a difference between the computed PACO value and a respective reference PACO value in the PACO-reference profile; and
outputting, by the comparison unit, the computed difference, the computed difference being indicative of a deviation of the state of the cell culture in the bioreactor from the reference state.

16. The method of claim 15, the PACO reference profile comprising a plurality of reference PACO values, the method further comprising calculating the reference PACO values by:
receiving a data object comprising the medium-specific relation;
repeatedly receiving, at a current time, a current CO2 off gas rate of the reference bioreactor in $$\left[\frac{mol}{min}\right]$$

and a current pH value of the medium of the reference bioreactor measured at said current time while cultivating the cell culture in the reference bioreactor;
computing, for each of the received pairs of a current CO2 off gas rate and a current pH value, one of the reference PACO values, the computation of the reference PACO value using as input:
the received current CO2 off gas rate of the reference bioreactor;
the received current pH value of the reference bioreactor;
the total gas inflow rate of the reference bioreactor at the time of receiving the current CO2 off gas rate; and
the medium-specific relation.

17. The method of claim 16, further comprising creating, the PACO-reference profile of the reference bioreactor by:
plotting the reference PACO values in a CO2 off gas rate versus time plot; and
fitting a curve in the plotted reference PACO values, said curve constituting the reference PACO profile.

18. The method of claim 16, the computation of each of the reference PACO values at respective current times comprising computing, for each of the received current CO2 off gas rates and pH values of the reference bioreactor:

an expected CO2 off gas fraction of a current outgas volume of the reference bioreactor according to: $FCO2_{R\text{-}EXP\text{-}ti}$ [%]=REL-M1 ($pH_{R\text{-}ti}$), wherein $FCO2_{R\text{-}EXP\text{-}ti}$ [%] is a predicted CO2 off gas fraction of the total off gas volume of the reference bioreactor in % at the current time, the prediction being calculated, by using the received current pH value as input for REL-M1 ($pH_{R\text{-}ti}$), wherein REL-M1 is the medium-specific relation of the medium, wherein $pH_{R\text{-}ti}$ is the current pH value in the medium of the reference bioreactor received at the time, an expected CO2 off gas rate value according to:

$$ACO_{R\text{-}\text{EXP}\text{-}ti}[\text{mol/min}] = \left(\frac{FCO2_{R\text{-}\text{EXP}\text{-}ti}\ [\%]}{100}\right) \times TGI_R\left[\frac{\text{mol}}{\text{min}}\right],$$

wherein the $ACO_{R\text{-}EXP\text{-}ti}$ [mol/min] value is the expected CO2 off gas rate of the reference bioreactor in $$\left[\frac{\text{mol}}{\text{min}}\right],$$

wherein the $TGI_R$ is the total amount of gas influx of the reference bioreactor at the current time, and the reference PACO value according to: $PACO_{R\text{-}ti}=ACO_{R\text{-}EXP\text{-}ti}$ [mol/min]$-ACO_{R\text{-}M\text{-}ti}$ [mol/min], wherein $PACO_{R\text{-}ti}$ [mol/min] is the reference PACO value at a given time, wherein $ACO_{R\text{-}M\text{-}ti}$ [mol/min] is the CO2 off gas rate in $$\left[\frac{\text{mol}}{\text{min}}\right]$$

measured at the given time in the reference bioreactor.

\* \* \* \* \*